(12) United States Patent
Maianti et al.

(10) Patent No.: US 10,640,767 B2
(45) Date of Patent: May 5, 2020

(54) ASSAY FOR EXO-SITE BINDING MOLECULES

(71) Applicant: President and Fellows of Harvard College, Cambridge, MA (US)

(72) Inventors: Juan Pablo Maianti, Revere, MA (US); David R. Liu, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/177,141

(22) Filed: Oct. 31, 2018

(65) Prior Publication Data

US 2019/0127732 A1    May 2, 2019

Related U.S. Application Data

(63) Continuation of application No. PCT/US2017/058722, filed on Oct. 27, 2017.

(60) Provisional application No. 62/414,640, filed on Oct. 28, 2016.

(51) Int. Cl.
| | | |
|---|---|---|
| *C12N 15/10* | (2006.01) | |
| *C40B 40/14* | (2006.01) | |
| *C40B 20/04* | (2006.01) | |
| *C40B 40/10* | (2006.01) | |

(52) U.S. Cl.
CPC .......... *C12N 15/1093* (2013.01); *C40B 40/10* (2013.01); *C40B 40/14* (2013.01); *C40B 20/04* (2013.01)

(58) Field of Classification Search
CPC ..... C12N 15/1093; C40B 40/14; C40B 40/10; C40B 20/04
See application file for complete search history.

(56) References Cited

U.S. PATENT DOCUMENTS

| | | |
|---|---|---|
| 7,070,928 B2 | 7/2006 | Liu et al. |
| 7,491,494 B2 | 2/2009 | Liu et al. |
| 8,975,232 B2 | 3/2015 | Liu et al. |
| 9,243,038 B2 | 1/2016 | Liu et al. |
| 10,053,725 B2 | 8/2018 | Liu et al. |

(Continued)

FOREIGN PATENT DOCUMENTS

WO    WO 2015/069876    5/2014

OTHER PUBLICATIONS

Tanaka et al. (Structural Insights into the Life History of Thrombin in Recent Advances in Thrombosis and Hemostasis, 2008, editors: K. Tanaka and E. W. Davie, Springer Japan KK, Tokyo, pp. 80-106) (Year: 2008).*

(Continued)

*Primary Examiner* — Jeremy C Flinders
(74) *Attorney, Agent, or Firm* — Wolf, Greenfield & Sacks, P.C.

(57) ABSTRACT

Methods for the identification of agents the bind to exo-sites of proteins are provided. Agents identified by the methods described herein and pharmaceutical compositions comprising the identified agents are also provided. Methods of using an identified agent for the treatment or prevention of a disease, disorder, or condition are also provided, including methods of treating or preventing a disease associated with reduced, elevated, or ectopic expression or aberrant activity of a protein comprising an exo-site.

17 Claims, 12 Drawing Sheets

Specification includes a Sequence Listing.

(56) References Cited

U.S. PATENT DOCUMENTS

| | | |
|---|---|---|
| 2004/0014140 A1 | 1/2004 | Erlanson et al. |
| 2014/0370008 A1* | 12/2014 | Huntington ............ C07K 16/36 424/133.1 |
| 2016/0193192 A1 | 7/2016 | Carmeliet et al. |
| 2016/0282364 A1 | 9/2016 | Kleiner et al. |

OTHER PUBLICATIONS

Hoen et al. (Anal. Biochem., 2012, 421:622-631) (Year: 2012).*
Shelton et al. (Proc. Natl. Acad. Sci., 2014, 106(48):20228-20233) (Year: 2014).*
PCT/US17/58722, Feb. 12, 2018, International Search Report and Written Opinion.
PCT/US17/58722, May 9, 2019, International Preliminary Report on Patentability.
International Search Report and Written Opinion for Application No. PCT/US17/58722 dated Feb. 12, 2018.
International Preliminary Report on Patentability for Application No. PCT/US17/58722 dated May 9, 2019.
Bentley et al., Accurate whole human genome sequencing using reversible terminator chemistry. Nature. Nov. 6, 2008;456(7218):53-9. doi: 10.1038/nature07517.
Brudno et al., An in vitro translation, selection and amplification system for peptide nucleic acids. Nat Chem Biol. Feb. 2010;6(2):148-55. doi: 10.1038/nchembio.280. Epub Dec. 27, 2009.
Buller et al., Design and synthesis of a novel DNA-encoded chemical library using Diels-Alder cycloadditions. Bioorg Med Chem Lett. Nov. 15, 2008;18(22):5926-31. doi: 10.1016/j.bmcl.2008.07.038. Epub Jul. 15, 2008.
Clark et al., Design, synthesis and selection of DNA-encoded small-molecule libraries. Nat Chem Biol. Sep. 2009;5(9):647-54. doi: 10.1038/nchembio.211. Epub Aug. 2, 2009. Erratum in: Nat Chem Biol. Oct. 2009;5(10):772.
Gartner et al., DNA-templated organic synthesis and selection of a library of macrocycles. Science. Sep. 10, 2004;305(5690):1601-5. Epub Aug. 19, 2004.
Halpin et al., DNA display I. Sequence-encoded routing of DNA populations. PLoS Biol. Jul. 2004;2(7):E173. Epub Jun. 22, 2004.
Halpin et al., DNA display II. Genetic manipulation of combinatorial chemistry libraries for small-molecule evolution. PLoS Biol. Jul. 2004;2(7):E174. Epub Jun. 22, 2004.
Halpin et al., DNA display III. Solid-phase organic synthesis on unprotected DNA. PLoS Biol. Jul. 2004;2(7):E175. Epub Jun. 22, 2004.
Hansen et al., A yoctoliter-scale DNA reactor for small-molecule evolution. J Am Chem Soc. Jan. 28, 2009;131(3):1322-7. doi: 10.1021/ja808558a.
Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.
Maianti et al., Anti-diabetic activity of insulin-degrading enzyme inhibitors mediated by multiple hormones. Nature. Jul. 3, 2014;511(7507):94-8. doi: 10.1038/nature13297. Epub May 21, 2014.
Mannocci et al., High-throughput sequencing allows the identification of binding molecules isolated from DNA-encoded chemical libraries. Proc Natl Acad Sci U S A. Nov. 18, 2008;105(46):17670-5. doi: 10.1073/pnas.0805130105. Epub Nov. 10, 2008.
Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120. Ho, Chun He [corrected to Ho, Chun Heen].
Melkko et al., Encoded self-assembling chemical libraries. Nat Biotechnol. May 2004;22(5):568-74. Epub Apr. 18, 2004.
Tse et al., Translation of DNA into a library of 13,000 synthetic small-molecule macrocycles suitable for in vitro selection. J Am Chem Soc. Nov. 19, 2008;130(46):15611-26. doi: 10.1021/ja805649f. Epub Oct. 29, 2008.
Berg et al., Enhanced protein C activation and inhibition of fibrinogen cleavage by a thrombin modulator. Science. Sep. 6, 1996;273(5280):1389-91.
Dennis et al., Peptide exosite inhibitors of factor VIIa as anticoagulants. Nature. Mar. 30, 2000;404(6777):465-70.
Gale et al., Molecular characterization of an extended binding site for coagulation factor Va in the positive exosite of activated protein C. J Biol Chem. 2002;277(32):28836-28840.
Kasanov et al., Characterizing Class I WW domains defines key specificity determinants and generates mutant domains with novel specificities. Chem Biol. 2001;8(3):231-241.
Lauer-Fields et al., Selective modulation of matrix metalloproteinase 9 (MMP-9) functions via exosite inhibition. J Biol Chem. Jul. 18, 2008;283(29):20087-95.
Lelais et al., Discovery of a potent covalent mutant-selective EGFR inhibitor—the journey from high throughput screening to EGF816. Proceedings of the 106th Annual Meeting of the American Association for Cancer Research; Apr. 18-22, 2015; Philadelphia, PA.: AACR; Cancer Res 2015;75(15 Suppl):Abstract nr 2585.
Lin et al., A high-throughput cell-based screening for L858R/T790M mutant epidermal growth factor receptor inhibitors. Anticancer Res. Jan. 2012;32(1):147-51.
Rettenmaier et al., A small-molecule mimic of a peptide docking motif inhibits the protein kinase PDK1. Proc Natl Acad Sci U S A. Dec. 30, 2014;111(52):18590-5.
Runyon et al., Structural and functional analysis of the PDZ domains of human HtrA1 and HtrA3. Protein Sci. 2007;16(11):2454-2471.
Schlundt et al., Proteomics analysis of Tsg101 ubiquitin-E2-like variant (UEV) interactions. Mol Cell Proteomics. Nov. 2009;8(11):2474-86.
Weng et al., Structure-function analysis of SH3 domains: SH3 binding specificity altered by single amino acid substitutions. Mol Cell Biol. Oct. 1995;15(10):5627-34.
Xu et al., Inhibition of MMP-2 gelatinolysis by targeting exodomain-substrate interactions. Biochem J. Aug. 15, 2007;406(1):147-55.
Yang et al., Discovery of a Potent Class of P13Kα Inhibitors with Unique Binding Mode via Encoded Library Technology (ELT). ACS Med Chem Lett. Mar. 20, 2015;6(5):531-6.

* cited by examiner

DNA sequencing analysis

| Sample | Total reads | Valid barcodes | |
|---|---|---|---|
| WT-IDE | 2,456,169 | 2,131,569 | 87% |
| A479L-IDE | 2,455,404 | 2,160,599 | 88% |
| WT heat | 2,070,373 | 1,837,363 | 89% |
| A479L heat | 2,154,568 | 1,917,879 | 89% |
| Input library | 2,397,703 | 2,059,888 | 86% |

FIGURE 2C

ASSAY FOR EXO-SITE BINDING MOLECULES

RELATED APPLICATIONS

This application claims priority under 35 U.S.C. §§ 120 and 365(c) to and is a continuation of international PCT Application, PCT/US2017/058722, filed Oct. 27, 2017, which claims priority under 35 U.S.C. § 119(e) to U.S. Provisional Patent Application, U.S. Ser. No. 62/414,640, filed Oct. 28, 2016, the entire content of each are incorporated herein by reference.

GOVERNMENT SUPPORT

This invention was made with government support under grant number GM065865 awarded by National Institutes of Health. The government has certain rights in the invention.

BACKGROUND

Screening methods for the identification of drug compounds are central to effective drug discovery. Accordingly, the efficiency and cost effectiveness of drug discovery can be improved by selection-based methods with higher throughput and lower infrastructure requirements as compared with many screening methods.

SUMMARY

The traditional approach for identification of agents that inhibit or otherwise modulate proteins relies on assays based on the protein's activity. For example, a library of inhibitors may be screened against a protease in a multi-well plate format through the detection of cleavage of a fluorogenic internally-quenched substrate that mimics the natural substrate. The identified inhibitors of the protease's cleavage activity typically interact, covalently or non-covalently, at or near the catalytic site and may outcompete native substrates by having a higher binding affinity for the protein. Identification of compounds that bind to sites other than the catalytic site, such as exo-sites (e.g., allosteric sites, distal binding pockets, regulatory sites, and non-catalytic domains), is significantly less likely using an activity-based assay reported by a small substrate mimic. Additionally, if an enzyme is responsible for the processing of multiple substrates in vivo, the outcomes that favorably modulate a disease by affecting activity with regard to one substrate cannot easily be separated from adverse effects due to the enzyme's pleiotropic action on other substrates. For example, small molecule inhibitors of insulin degrading enzyme (IDE) may improve insulin signaling by inhibiting proteolysis of insulin but may cause adverse effects such as increased blood sugar levels by inhibiting proteolysis of glucagon by IDE. Screening assays relying on a fluorogenic insulin or glucagon mimic may be unsuitable for identifying a selective inhibitor for insulin degradation that does not also inhibit glucagon degradation, or inhibits it to a lesser extent. Protein-substrate interactions at sites other than the catalytic site may modulate the activity or selectivity of proteins in the case of proteins that process multiple substrates. Such sites may be referred to as exo-sites, distal binding pockets, allosteric sites, regulatory sites, or non-catalytic domains. Herein we use the term exo-site as the most general definition that embodies all binding sites for molecules that are typically distinct from the catalytic site, but binding of a compound at the site may affect the activity of the protein, particularly the catalytic activity and/or binding of substrates near the pocket.

Affinity based selection methods may also be more suitable than screens employing activity based assays for discovery of agents that interact with proteins away from the active site, such as at exo-sites. Such methods may be suitable for discovery of agents that are intended to modulate protein selectivity rather than to behave as competitive inhibitors for native substrates. High-throughput selection on diverse libraries can identify novel exo-site binding site agents or scaffolds, and may also be used to identify unknown protein-agent interactions at previously unknown exo-sites and other orphan binding pockets beyond the active site.

In one aspect, the present disclosure provides methods, compositions, and systems useful for identifying agents that interact with exo-sites of a protein, distal binding pockets, allosteric sites, or non-catalytic domains. Agents identified by the methods and systems described herein may be used as pharmaceutical agents for the treatment of a disease associated with the protein or may be used in the design and development of a pharmaceutical agent. Agents identified may also be used as development leads for further drug design and discovery of pharmaceuticals that target exo-sites of a protein, distal binding pockets, allosteric sites, or non-catalytic domains. The method typically involves performing a screen of a library of agents using two variants of a protein, wherein the two variants have a structural difference that fills or changes the shape of the three-dimensional shape of the exo-site pocket of the protein. Typically one protein variant includes a wild type exo-site, and the other variant includes a mutated exo-site. For example, in certain embodiments, a first variant may be the wild-type protein, and a second variant may be a mutant with a "bump" due to a sequence variation at the exo-site. The "bump" in the exo-site will influence the binding of candidate agents at the exo-site. By comparing the binding of the candidate agents to the exo-site of the wild-type protein versus that of the mutant, candidate agents that have greater binding for the wild-type protein can be identified as agents that bind in the exo-site. Alternatively, the binding or enrichment measurement results for the mutant variant can be applied as a mathematical penalty for calculations using the binding or enrichment measurement results from the wild-type variant. The mathematical penalty may be derived from subtraction, division, multiplication, or similar operation with the data. The outcome of applying the calculation for all library members is to preferentially highlight the exo-site binders, or conversely lower the signal of the non-exo-site binders, improve the noise-signal ratio of non-specific binders, or lower the stochastic background noise to facilitate hit-calling of exo-site binders.

Agents identified using the methods described herein may be further characterized using any assays and methods known in the art, for example, biochemical assays, southwestern blotting, western blotting, activity-based probes, capillary electrophoresis, affinity chromatography, competition studies, siRNA studies, in vitro cytotoxicity studies, in vivo animal model studies, etc. The methods of identifying agents that bind to an exo-site are amenable to high-throughput screening techniques including robotic assisted fluid delivery, combinatorial chemistry, microfluidics, and computer analysis of the resulting data. In certain embodiments, a collection of compounds such as a combinatorial library may be provided for screening. In other embodiments, a historical collection of chemical compounds may screened using the inventive methods. The methods may also be used to test one candidate compound at a time.

Provided herein are methods of identifying and facilitating the de novo discovery of agents that binds an exo-site of a protein, the method comprising providing a first variant of the protein, wherein the protein comprises an exo-site; providing a second variant of the protein, wherein the exo-site of the second variant comprises at least one different amino acid (e.g., substitution, deletion, or addition) than the exo-site of the first variant; contacting a candidate agent with each of the first and second variants; determining an enrichment-dependent parameter of the candidate agent to each of the first and second variants through a one-pot library binding or enrichment assay; comparing (e.g., by visual or mathematic procedures) the results of a candidate agent binding to the first variant with the binding to the second variant, wherein if the enrichment-based parameter using the first protein variant is greater than the enrichment-based parameter using the second protein variant, then the candidate agent is identified as an agent that binds an exo-site of the protein. In certain embodiments, the protein is an enzyme (e.g., protease). In certain embodiments, the method is performed on a library of candidate agents. The agents may be screened in a high-throughput format that allows for the screening of tens, hundreds, thousands, millions, or even billions of candidate agents in parallel. In certain embodiments, the method involves computation, mathematical operations, additive smoothing, or statistical treatments to compare the enrichment-based parameters from the two variants. In certain embodiments, the mathematical operation involves subtraction, division, or multiplication of a library member's enrichment-based parameter obtained the presence of one variant ($E_1$) versus the second variant ($E_2$). In certain embodiments the mathematical operations are: $E_1-E_2$; or $E_1/E_2$; or $x.E_1-y.E_2$; or $x.E_1/y.E_2$; or $x.E_1^a-y.E_2^b$; or $x.E1^a/y.E2^b$; or $(x.E_1^a-y.E_2^b)^c$; or $(E1^a/E2^b)^c$, where x, y, a, b and c represent variable coefficients.

In certain embodiments, the exo-site is a binding pocket that modulates the interactions of the protein with one or more substrates, one or more metabolites, one or more binding partners, or one or more native partners of the protein when an agent is bound to the exo-site. In certain embodiments, the exo-site comprises a binding pocket that modulates the substrate selectivity or binding preferences of the protein when an agent is bound to the exo-site. In certain embodiments, the exo-site comprises a binding pocket defined by amino acids that are at least about 2, 3, 5, 10, 15, 20, 25, 30, 35, 40, 45, or 50 angstroms away from the amino acids of the protein's active site. In some embodiments, the amino acids of the protein active site are the amino acids that participate in catalysis at the protein's active site (e.g., catalytic site). In certain embodiments, the exo-site comprises a binding pocket defined by amino acids that can be replaced with different amino acids without significantly altering the activity of the protein, for example, wherein the activity of the protein is not significantly altered if the $K_m$ or $V_{max}$ is altered by a factor of between about 1.1-fold and about 10-fold for the same substrate and under the same assay conditions. In certain embodiments, the amino acids of the exo-site are typically not directly involved in catalysis of biochemical steps, transition state stabilization, substrate, or cofactor binding. In certain embodiments, the stability and activity over time for the variants is similar by a factor of between about 1.1-fold and about 10-fold.

In certain embodiments, the first variant of the protein is a wild-type protein or truncated variant of the wild-type protein. In certain embodiments, the first variant includes a wild-type exo-site. In certain embodiments, the second variant comprises a mutant of the first variant, wherein one amino acid of the exo-site in the first variant is replaced with a different amino acid in the second variant. In some embodiments, the replacement amino acid in the second variant comprises an amino acid side chain with a higher number of non-hydrogen atoms (e.g., C, N, O, S) than the replaced amino acid in the first variant. For example, an alanine in the exo-site is replaced with a leucine in the second variant. In certain embodiments, the first and second variants are two different isoforms of a protein or truncated variant of two different isoforms.

Any type of molecules may be screened in a library format to identify exo-site binders. For example, small molecules, nucleic acids, saccharides, polysaccharides, peptides, proteins, organic molecules, organometallic molecules, etc. may be screened using the inventive methods and systems. In certain embodiments, a library of agents is screened. In certain embodiments, the library is a library of small molecules. In certain embodiments, the library is a library of polynucleotides, polypeptides, or polysaccharides. In certain embodiments, the library is an encoded library. In some embodiments, the library is a DNA-encoded library. In some embodiments, the step of contacting comprises incubating the encoded candidate agents with each of the first and second variants in series or in parallel. The method may further comprise amplifying the DNA codons of DNA-encoded agents by PCR, optionally wherein the PCR primers are encoded to identify the compound to which it is attached. In some embodiments, the method further comprises sequencing the PCR amplified DNA. In certain embodiments, the step of determining binding comprises measuring the relative or absolute library member sequence abundance for the candidate agent DNA coding sequences. In certain embodiments, the step of determining binding comprises measuring an enrichment of post-selection sequence abundance for the candidate agent codons over pre-selection sequence abundance. In certain embodiments, the step of comparing comprises comparing the measured enrichment in sequence abundance for each candidate agent after incubation with the first variant with the measured enrichment in sequence abundance after incubation with the second variant. In certain embodiments, the method involves computation, mathematical operations, additive smoothing, or statistical treatments to compare the enrichment-based parameters from the two variants. In certain embodiments, the mathematical operation involves subtraction, division, or multiplication of a library member's enrichment-based parameter obtained the presence of one variant ($E_1$) versus the second variant ($E_2$). In certain embodiments the mathematical operations are: $E_1-E_2$; or $E_1/E_2$; or $x.E_1-y.E_2$; or $x.E_1/y.E_2$; or $x.E_1^a-y.E_2^b$; or $x.E1^a/y.E2^b$; or $(x.E_1^a-y.E_2^b)^c$; or $(E1^a/E2^b)^c$, where x, y, a, b and c represent variable coefficients.

In another aspect, the present disclosure provides an agent that binds an exo-site of a protein identified by a method described herein. The disclosure also provides pharmaceutical compositions comprising an agent that binds an exo-site of a protein identified by a method described herein.

In another aspect, the present disclosure provides a method of treating or preventing a disease, disorder, or condition in a subject in need thereof, the method comprising administering to the subject a therapeutically effective amount of an agent that binds an exo-site of a protein as identified by a method described herein, or a pharmaceutically acceptable salt, or pharmaceutical composition thereof. In certain embodiments, the disease, disorder, or condition is associated with reduced, elevated, or ectopic expression/activity of a protein with an exo-site. In certain embodiments, the disease, disorder, or condition is associated with the aberrant activity of a protein with an exo-site.

Any protein such as an enzyme may be used in accordance with the invention. The protein may or may not be known to have an exo-site (e.g., distal binding pocket, allosteric site, or non-catalytic domain) and its function may or may not be known or assigned (orphan exo-site). In certain embodiments, the protein being used in the inventive method is insulin degrading enzyme (IDE). In certain embodiments, the agent binds an exo-site of IDE. In certain embodiments, the method of treating a disease, disorder, or condition is for a disease, disorder, or condition associated with reduced, elevated, or ectopic expression/activity of IDE. In certain embodiments, the method of treating a disease, disorder, or condition is for a disease, disorder, or condition associated with aberrant activity of IDE. In some embodiments, the protein is IDE, and the disease is metabolic disorder. In some embodiments, the metabolic disorder is diabetes. In some embodiments, the metabolic disorder is hyperglycemia, impaired glucose tolerance, obesity, sodium imbalance, or hypertension.

The details of certain embodiments of the invention are set forth in the Detailed Description of Certain Embodiments, as described below. Other features, objects, and advantages of the invention will be apparent from the Definitions, Detailed Description, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

FIG. 2C shows DNA sequencing reads for each sample analyzed by Illumina MiSeq single-end 50 read run.

FIG. 5A shows the X-ray co-crystal structure of IDE bound to macrocyclic inhibitor 6b (2.7 Å resolution, Protein Data Bank entry: 4LTE). Macrocycle 6b is represented as a ball-and-stick model, and the catalytic zinc atom is represented as a sphere in the indicated catalytic active site. FIG. 5B shows the relative position of macrocycle 6b bound 11 Å from the catalytic zinc atom. FIG. 5C shows the electron density map (composite omit map contoured at 1σ) and model of IDE-bound macrocycle 6b interacting with a 10 Å-deep hydrophobic pocket. FIG. 5D and FIG. 5E show activity assays for wild-type or mutant human IDE variants in the presence of 6bK. FIG. 5F shows a view of the exo-site of IDE with macrocycle 6b bound with the mutated residues from FIG. 5D and FIG. 5E labeled.

DETAILED DESCRIPTION OF CERTAIN EMBODIMENTS

Figure 1A:
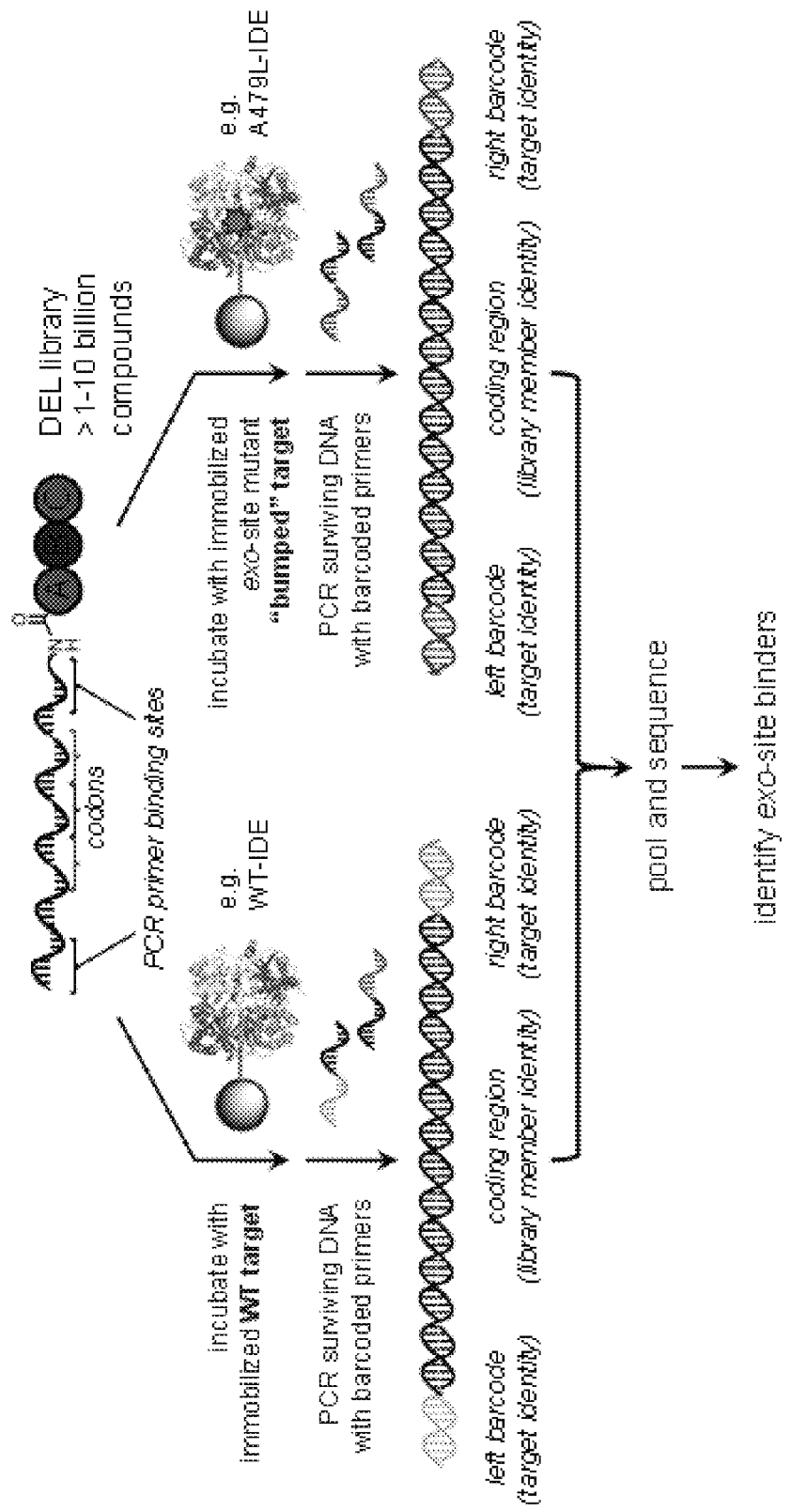
FIG. 1A is a scheme showing an exemplary identification strategy for the discovery of distal or exo-site binding agents of insulin degrading enzyme (IDE) by comparison of in vitro selections of DNA-encoded libraries performed against a wildtype variant (e.g., N-His$_6$-IDE) and an exo-site "bumped" mutant variant (shown as an orange star, e.g., N-His$_6$-A479L-IDE).

The present disclosure provides methods, compositions, and systems for identifying an agent that binds an exo-site of a protein. An exo-site is a secondary binding site, remote from the catalytic site, on a protein. Also provided are agents that bind an exo-site of a protein as identified by the inventive method, pharmaceutical compositions comprising the agent, methods of treating a disease using the agent, and methods of modulating the selectivity or activity of a protein using the agent, wherein the agent is identified by a method described herein. In certain embodiments, the protein is an enzyme.

In one aspect, the disclosure provides methods of identifying an agent that binds an exo-site of a protein. The method typically involves comparison of the binding of a candidate agent to two (or more) variants of a protein: a first variant, wherein the protein comprises an exo-site; and a second variant, which also includes the exo-site, but the exo-site of the second variant differs from the exo-site of the first variant. The second variant may differ from the first variant in the presence of a "bump" or other feature in the exo-site binding pocket. The "bump" may consist of one or more amino acid side chains present in the second variant that differ from side chains present in the first variant. Without wishing to be bound by any particular theory, the "bump" may impair or otherwise affect the binding of an agent to the exo-site in the second variant relative to the binding of the agent to the exo-site in the first variant. The "bump" may impair binding by, for example, altering the steric environment of the exo-site (e.g., by taking up volume in the exo-site binding pocket which the agent would otherwise occupy), altering specific binding interactions between the exo-site and an agent (e.g., by disrupting hydrogen bonding that would otherwise form between an exo-site residue and the agent), or by changing the hydrophobic/hydrophilic character of the exo-site (e.g., by introducing a more or less polar side chain in the exo-site).

The first and second variant may be variants of the same protein or of related proteins. Typically the variants are variants of the same protein. In some embodiments, the second variant is a mutant of the first variant. First and second variants that are isoforms of the same protein or truncated versions of different isoforms of a protein are also contemplated. Without wishing to be bound by a particular theory, different isoforms of a protein with an exo-site may display high evolutionarily conservation for sequences or residues that comprise the catalytic site, which are required for biochemical steps, but less evolutionary conservation for sequences or residues comprising the exo-site. Thus the method may be useful for identifying binding agents that display high specificity for the exo-site in one or more isoforms of a protein among a family of evolutionarily related proteins. In some embodiments, the first and second variants are different isoforms of a protein or truncated variants of different isoforms of a protein. Other differences between the first and second variant are also contemplated, such as a second variant that is prepared by a chemical modification of a first variant. In some embodiments, the first variant is a wild-type protein or a truncated variant of a wild-type protein. In some embodiments, the first variant is not a wild-type protein or truncated variant of a wild-type protein. In some embodiments, the second variant is a wild-type protein or truncated variant of a wild-type protein. In some embodiments, the second variant is not a wild-type protein or a truncated variant of a wild-type protein. In some embodiments, the first and second variants are proteins from the same species. In some embodiments, the first and second variants are proteins from different species. In some embodiments, the first and second variants are proteins that result in different phenotypes, for example, a first variant resulting in a healthy or normal phenotype, prevention or improvement of a disease phenotype, and a second variant resulting in a phenotype associated with a disease, disorder, adverse effect or condition associated with the protein.

The first and second variant may only differ by one or more changes in the exo-site (e.g., one or more amino acid mutations) or may have additional differences. In some embodiments, the first and second variant are identical or homologous except for the mutation of a single amino acid of the exo-site. In some embodiments, the first and second variant are identical except for the mutation of between one and two, one and three, one and five, two and five, or five and ten amino acids of the exo-site. In some embodiments, the first and second variant have homologous protein sequences with at least 80%, at least 85%, at least 90%, at least 91%, at least 92%, at least 93%, at least 94%, at least 95%, at least 96%, at least 97%, at least 98%, at least 99%, or at least 99.5% sequence identity.

A second variant that is a mutant may be provided by any method known in the art, as the disclosure is not limited in that way. For example, a mutant may be a naturally occurring variant of the wild-type protein, may be prepared by chemical peptide synthesis, chemical modification of a first variant, or may be prepared by mutagenesis (e.g., site-directed mutagenesis). In some embodiments, the mutant is provided by recombinant expression of a mutant gene construct in host cells.

The second variant (e.g., mutant, isoform, homolog) has at least one different amino acid in the exo-site compared with the exo-site of the first variant (e.g., wild-type, isoform, homolog). In some embodiments, one amino acid of the exo-site of the first variant is replaced with a different amino acid in the second variant. In some embodiments, two amino acids of the exo-site of the first variant are replaced with different amino acids in the second variant. In some embodiments, three or more amino acids of the exo-site of the first variant are replaced with different amino acids in the second variant.

The difference of the exo-site between the first and second variant may also be due to a deletion or addition of an amino acid. In some embodiments, one or more amino acids of the exo-site of the first variant are removed from the exo-site in the second variant. In some embodiments, one or more amino acids of the exo-site of the first variant are added to the exo-site in the second variant. The difference of the exo-site between the first and second variant may also involve chemical modification of an amino acid of the exo-site. For example, an exo-site amino acid with a reactive group (e.g., carboxylic acid, hydroxyl, thiol, amide) may be synthetically modified to a form a covalent bond with a small molecule. In some embodiments, one or more amino acids of the exo-site of the first variant are chemically modified in the second variant. In some embodiments, the one or more modified amino acids in the second variant are proteinogenic amino acids. In some embodiments, one or more of the modified amino acids in the second variant are non-proteinogenic amino acids. The term "proteinogenic" refers to the 23 amino acids that can be incorporated into proteins during translation, including the 20 amino acids of the standard genetic code and selenocysteine, pyrrolysine, and N-formylmethionine. In some embodiments, the proteinogenic amino acid is one of the 20 amino acids of the standard genetic code.

The different amino acid(s) in the exo-site of the second variant may be an amino acid with a side chain that is larger than the side chain of the corresponding residue(s) in the first variant. In some embodiments, the replacement amino acid in the second variant comprises a side chain with a higher number of non-hydrogen atoms (e.g., the total number of C, N, O, and S atoms) than the replaced amino acid in the first variant. In some embodiments, the replacement amino acid(s) in the second variant comprises a side chain with a lower number of non-hydrogen atoms than the replaced amino acid(s) in the first variant. The side chain of the different amino acid may also differ from the side chain of the corresponding amino acid in the first variant by having a different charge or hydrophobicity. In some embodiments, the replacement amino acid in the second variant comprises a side chain with a higher ionic charge than the corresponding amino acid in the first variant (e.g., a positively charged side chain in place of a neutral or negatively charged side chain, a neutral side chain in place of a negatively charged side chain). In some embodiments, the replacement amino acid in the second variant comprises a side chain with a lower ionic charge than the corresponding amino acid in the first variant (e.g., a negatively charged side chain in place of a neutral or positively charged side chain, a neutral side chain in place of a positively charged side chain). In some embodiments, the replacement amino acid in the second variant comprises a polar side chain and the corresponding amino acid in the first variant comprises a non-polar side chain. In some embodiments, the replacement amino acid in the second variant comprises a non-polar side chain and the corresponding amino acid in the first variant comprises a polar side chain. Amino acids with positively charged side chains include arginine, histidine, and lysine. Amino acids with negatively charged side chains amino acids include aspartate and glutamate. Neutral amino acid side chains include those in serine, threonine, asparagine, glutamine, cysteine, glycine, proline, alanine, leucine, isoleucine, methionine, phenylalanine, tryptophan, tyrosine, and valine. Polar amino side chains include those with positively and negatively charged side chains and serine, threonine, asparagine, glutamine, cysteine, methionine, and tyrosine. Amino acids with non-polar or hydrophobic side chains include glycine, proline, alanine, isoleucine, leucine, phenylalanine, valine, and tryptophan.

The methods described herein provide a means of identifying an agent that binds an exo-site. An exo-site refers to a site of a protein that is not an active site or catalytic site, i.e., not a site at which a substrate is modified. An exo-site may also be referred to as a distal site or distal binding pocket. In some embodiments, an exo-site is a distal binding pocket. In some embodiments, an exo-site is not a distal binding pocket. Both exo-sites and allosteric site may refer to binding sites that regulate a protein and are distinct from the catalytic site. In some embodiments, an exo-site is an allosteric site. In some embodiments, an exo-site is not an allosteric site. In certain embodiments, an exo-site is on the surface of a protein. In some embodiments, a protein may adopt one or more conformations wherein an exo-site is on the surface of the protein. In other embodiments, a protein may adopt one or more conformations wherein the exo-site is not on the surface of the protein.

Exo-site binding may modulate interactions of the protein with one or more substrates, one or more metabolites, or one or more native partners of the proteins (e.g., protein, peptide, polynucleotide, small molecule, or carbohydrate). In some embodiments, the binding of an agent to the exo-site imparts selectivity to the protein between two or more substrates, two or more metabolites, or two or more native partners of the protein. In some embodiments, the binding of an agent to the exo-site alters the selectivity of the protein for two or more substrates, two or more metabolites, or two or more native partners of the protein.

Exo-site binding may modulate the activity of a protein, e.g., an enzyme. In some embodiments, an exo-site is a site that modulates the activity of the enzyme, e.g., the catalytic activity of the protein. In some embodiments, binding of an agent to an exo-site inhibits activity of the enzyme. In some embodiments, binding of an agent to an exo-site promotes activity of the enzyme. An enzyme may require a molecule, peptide, protein, or other agent to occupy one or more exo-sites in order for the enzyme to have activity, e.g., activity for modification of a substrate at the active site. In some embodiments, the enzyme is essentially inactive if the exo-site is unoccupied. In some embodiments, the activity of the enzyme is not dependent on whether the exo-site is occupied. In some embodiments, binding of an agent to an exo-site alters the $K_m$, $k_{cat}$, and/or $V_{max}$ of the enzyme as compared to the exo-site unoccupied or bound to another agent. In some embodiments, binding of an agent to an exo-site alters the $k_{cat}/K_m$ of the enzyme as compared to the exo-site unoccupied or bound to another agent. In some embodiments, the binding of an agent to the exo-site partially inhibits the activity of the protein, e.g., an enzyme, by at least 10%, at least 25%, at least 50%, at least 75%, at least 90%, at least 95%, at least 96%, at least 97%, at least 98%, at least 99%, or at least 99.5%.

Exo-site binding may also affect the selectivity of a protein (e.g., enzyme) for different substrates. The binding of an agent to an exo-site may increase the selectivity of an enzyme for the binding and/or modification (e.g., cleavage, oxidation, reduction, coupling, isomerization) of a particular substrate relative to one or more other substrates, or may decrease the selectivity of an enzyme for binding and/or modification of a particular substrate relative to one or more other substrates. For example, binding of an agent to an exo-site of insulin degrading enzyme (IDE) may increase the selectivity of IDE for catabolism of insulin versus glucagon. IDE degrades several substrates including, but not limited to, insulin, glucagon, amylin, calcitonin-gene related peptide (CGRP), amyloid beta-peptide, TGF-alpha, β-endorphin, somatostatin, and atrial natriuretic peptide. In some embodiments, the binding of an agent to the exo-site of IDE increases the selectivity of IDE for catabolism of a first IDE substrate over a second IDE substrate, wherein the substrates are selected from the group consisting of insulin, glucagon, amylin, calcitonin-gene related peptide (CGRP), amyloid beta-peptide, TGF-alpha, β-endorphin, somatostatin, and atrial natriuretic peptide.

Possible substrates of a protein with an exo-site as discussed herein include, but are not limited to, small molecules, proteins, hormones, polypeptides, metabolites, amino acids, lipids, signaling molecules, redox shuttles, nucleic acids, polynucleotides, nucleotides, nucleobases, carbohydrates, polysaccharides, monosaccharides, and cofactors. Substrate selectivity may be between two substrates of the same type (e.g., two polypeptides, two peptides, two small molecules) or between different kinds of substrates (e.g., a polypeptide and a small molecule). Generally, substrates may differ with regard to several characteristics, such as size, charge, conformation, or hydrophobicity. Proteins and polypeptides may differ in, for example, chain length, size, volume, charge, sequence, folding stability, number or location of disulfide bonds, isoform, and/or by one or more post-translational modifications. Lipids may differ in, for example, chain length, size, degree of saturation, headgroup, charge, or the number, type, and/or location of substituents. Nucleic acids and polynucleotides may differ in, for example, sequence, sequence length, sugar backbone (e.g., deoxyribose, ribose), base modification (e.g., methylation), and/or by differences in secondary structure (e.g., single strand vs. double strand, conformation). Carbohydrates may differ in, for example, chain length, substitution pattern, linkage pattern, epimerization, and/or charge. Signaling molecules, metabolites, amino acids, and other small molecules may differ in, for example, molecular weight, size, volume, degree of saturation, charge, degree of oxidation, degree of protonation, conformation, and/or the number, type, and/or location of substituents.

An exo-site may be defined in various ways. For example, the exo-site may be defined by the distance of the exo-site from the protein's active site or catalytic site. The exo-site may be defined by the amino acids surrounding a binding pocket. A binding pocket may have or comprise several regions or features including, but not limited to, hydrophobic patches, hydrophobic pockets, hydrophilic patches, hydrophilic pockets, amphiphilic patches, hydrogen bond donors, hydrogen bond acceptors, amphiphilic pockets, metal ions, or post-translational modifications. In some embodiments, the exo-site comprises a binding pocket defined by amino acids. In some embodiments, the amino acids defining the binding pocket are at least about 2 angstroms away from the amino acids of the protein's catalytic site. In some embodiments, the amino acids defining the binding pocket are at least about 3 angstroms away from the amino acids of the protein's catalytic site. In some embodiments, the amino acids defining the binding pocket are at least about 5 angstroms away from the amino acids of the protein's catalytic site. In some embodiments, the amino acids defining the binding pocket are at least about 10 angstroms away from the amino acids of the protein's catalytic site. In some embodiments, the amino acids defining the binding pocket are at least about 15 angstroms away from the amino acids of the protein's catalytic site. In some embodiments, the amino acids defining the binding pocket are at least about 20 angstroms away from the amino acids of the protein's catalytic site. In some embodiments, the amino acids defining the binding pocket are at least about 25 angstroms away from the amino acids of the protein's catalytic site. In some embodiments, the amino acids defining the binding pocket are at least about 30 angstroms away from the amino acids of the protein's catalytic site. In some embodiments, the amino acids defining the binding pocket are at least about 35, 40, 45, 50, 55, 60, 65, 70, 75, 80, 85, 90, 95 or 100 angstroms away from the amino acids of the protein's catalytic site.

The distance from the catalytic site may be measured as nearest atom-to-atom distance between amino acid residues of the exo-site and amino acid residues of the catalytic site, a metal ion of the catalytic site, a cofactor, or a co-substrate. For the purposes of the measurement the amino acids of the catalytic site may be defined in different ways. In some embodiments, the amino acids of the protein's catalytic site are the amino acids that surround the active site binding pocket, e.g., the binding pocket for one or more target substrates. In certain embodiments, the amino acids of the protein's catalytic site bind a substrate. In some embodiments, the amino acids of the protein's catalytic site are the amino acids that assist in catalysis. In some embodiments, the amino acids of the protein catalytic site are the amino acids that bind a cofactor. In some embodiments, the amino acids of the protein catalytic site are the amino acids that bind an active site metal ion. In some embodiments, the amino acids of the protein catalytic site are the amino acids that participate in substrate modification. In some embodiments, the amino acids of the protein's catalytic site are the amino acids that transfer protons, electrons, atoms, or groups of atoms (e.g., a functional group) to or from a substrate. In some embodiments, amino acids of the protein's catalytic site are the amino acids that form covalent, ionic, or hydrogen bonds with a substrate. In some embodiments, amino acids of the protein's catalytic site are the amino acids that catalyze chemical steps at the protein's catalytic site.

The distance from the active site may also be measured as nearest atom to atom distance between atoms of the exo-site binding agent and amino acid residues of the catalytic site, a metal ion of the catalytic site, a cofactor, or a co-substrate. For the purposes of the measurement the amino acids of the active site may be defined in different ways, as described above. In some embodiments, the atoms of the exo-site binding agent are at least about 2 angstroms away from the amino acids of the protein's catalytic site. In some embodiments, the amino acids defining the binding pocket are at least about 3 angstroms away from the amino acids of the protein's catalytic site. In some embodiments, the atoms of the exo-site binding agent are at least about 5 angstroms away from the amino acids of the protein's catalytic site. In some embodiments, the atoms of the exo-site binding agent are at least about 10 angstroms away from the amino acids of the protein's catalytic site. In some embodiments, the atoms of the exo-site binding agent are at least about 15 angstroms away from the amino acids of the protein's catalytic site. In some embodiments, the atoms of the exo-site binding agent are at least about 20 angstroms away from the amino acids of the protein's catalytic site. In some embodiments, the atoms of the exo-site binding agent are at least about 25 angstroms away from the amino acids of the protein's catalytic site. In some embodiments, the atoms of the exo-site binding agent are at least about 30, 35, 40, 45, 50, 55, 60, 65, 70, 75, 80, 85, 90, 95 or 100 angstroms away from the amino acids of the protein's catalytic site.

The protein's catalytic site may have a spherical or roughly spherical volume that extends from its center and has a radius of about 5 angstroms, about 6 angstroms, about 7 angstroms, about 8 angstroms, about 9 angstroms, about 10 angstroms, about 11 angstroms, about 12 angstroms, about 13 angstroms, about 14 angstroms, about 15 angstroms, about 16 angstroms, about 17 angstroms, about 18 angstroms, about 19 angstroms, about 20 angstroms, about 21 angstroms, about 22 angstroms, about 23 angstroms, about 24 angstroms, about 25 angstroms, about 26 angstroms, about 27 angstroms, about 28 angstroms, about 29 angstroms, or about 30 angstroms. The protein's active site may have a spherical or roughly spherical volume that extends from its center and has a radius of at least about 5 angstroms, at least about 6 angstroms, at least about 7 angstroms, at least about 8 angstroms, at least about 9 angstroms, at least about 10 angstroms, at least about 11 angstroms, at least about 12 angstroms, at least about 13 angstroms, at least about 14 angstroms, at least about 15 angstroms, at least about 16 angstroms, at least about 17 angstroms, at least about 18 angstroms, at least about 19 angstroms, at least about 20 angstroms, at least about 21 angstroms, at least about 22 angstroms, at least about 23 angstroms, at least about 24 angstroms, at least about 25 angstroms, at least about 26 angstroms, at least about 27 angstroms, at least about 28 angstroms, at least about 29 angstroms, at least about 30 angstroms, at least about 40 angstroms, or at least about 50 angstroms.

In certain embodiments, a protein may adopt one or more conformations that alter the distance between an exo-site of the protein and the protein's active site or catalytic site. In some embodiments, one conformation of a protein may result in an exo-site of the protein being of closer proximity to the protein's catalytic site (e.g., about 10 angstroms), while another conformation results in the exo-site being more distal to the protein's catalytic site (e.g., at least about 20 angstroms).

An exo-site may be fully distinct from the active site, for example, the exo-site and active site may not share any space within the protein, for example, the exo-site may be in a different subunit of the protein. Alternatively, the exo-site or distal site may be a smaller region or pocket of a space that also contains the active site. In such a case, substrates of the protein may bind to the region of the space associated with the active site, whereas exo-site binding agents bind to a different region or regions of the space. In some embodiments, the amino acids defining the exo-site and the amino acids defining the active may share one or more amino acid residues in common. In some embodiments, the amino acids defining the exo-site and the amino acids defining the active site do not share any amino acids.

Modifications or mutations to amino acids in a protein active site typically reduce or eliminate catalytic activity of the protein. Whereas, without wishing to be bound by theory, modifications or mutation to amino acids in an exo-site may not significantly alter the catalytic activity of a protein particularly for proteins that do not require occupation of the exo-site to be active. In certain embodiments, as would be appreciated by one of skill in the art, the activity of the protein may not be affected for a particular substrate but may be affected for another substrate. In some embodiments, an exo-site comprises a binding pocket defined by amino acids that can be replaced with different amino acids without significantly altering the activity of the protein. Altering includes increasing or decreasing protein activity, as well as changes in protein selectivity with respect to one or more substrates. In some embodiments, the activity of a protein with at least one modified or mutated exo-site amino acid is considered not significantly altered if the activity or selectivity of the protein is the same as the activity or selectivity of the protein before modification or mutation (e.g., the activities are not measurably different).

Significantly altered activity may be defined in terms of a change in $K_m$, $k_{cat}$, and/or $V_{max}$ for the activity of a protein on a given substrate under the same assay conditions for the modified protein versus the unmodified protein or control. In some embodiments, the activity of a protein with at least one modified or mutated exo-site amino acid is considered not significantly altered if $K_m$, $k_{cat}$, and/or $V_{max}$ is altered by a factor of between about 1.1-fold and about 10-fold for the same substrate and under the same assay conditions, in comparison between the modified and unmodified protein. In some embodiments, $K_m$, $k_{cat}$, and/or $V_{max}$ is increased by between about 1.1 fold and about 10-fold, about 1.1 fold and about 8-fold, about 1.1 fold and about 6-fold, about 1.1 fold and about 4-fold, or about 1.1 fold and about 2-fold. In some embodiments, $K_m$, $k_{cat}$, and/or $V_{max}$ is decreased by between about 1.1 fold and about 10-fold, about 1.1 fold and about 8-fold, about 1.1 fold and about 6-fold, about 1.1 fold and about 4-fold, or about 1.1 fold and about 2-fold. In some embodiments, the activity of a protein with at least one modified or mutated exo-site amino acid is considered not significantly altered if the activity or selectivity of the protein is at least about 95%, 90%, 80%, 70%, 60%, 50%, 25%, or 10% of the activity or selectivity of the protein before modification or mutation. In some embodiments, the activity of a protein with at least one modified or mutated exo-site amino acid is considered not significantly altered if the activity or selectivity of the protein is less than about 95%, 90%, 80%, 70%, 60%, 50%, 25%, or 10% of the activity or selectivity of the protein before modification or mutation. In some embodiments, the activity of a protein with at least one modified or mutated exo-site amino acid is considered not significantly altered if the activity or selectivity of the protein is at most about 110%, 150%, 200%, 300%, 400%, 500%, 750%, or 1000% of the activity or selectivity of the protein before modification or mutation. Combinations of these ranges are also contemplated, including protein activities between about 10% and 1000%, 25% and 500%, 70% and 200%, and 90% and 150%, though other ranges and endpoints are also considered.

The protein for which an exo-site binding molecule is to be identified may be a protein with a known exo-site. The exo-site may have been previously identified, and in some cases, other exo-site binding agents may be known. In certain embodiments, it may not be known whether the protein has an exo-site. The second variant of the protein may be modified or mutated at one or more amino acids in a known cavity on the surface of a protein or region of anactive site which is suspected of being a possible exo-site. In certain embodiments, no specific site of the protein is targeted, but there are sequence differences between the variants (e.g., two isoforms, random mutation). Thus, the method of identifying an exo-site binding agent may also be a method of de novo discovery of an exo-site. The location of a sequence difference may be used to identify the location of a binding pocket for variants that demonstrate different binding of one or more candidate agents.

Any kind of agent may be found to bind to an exo-site. In certain embodiments, the agent is a small molecule or a salt thereof. In some embodiments, the small molecule has a molecular weight of between about 100 Da and about 500 Da. In some embodiments, the small molecule has a molecular weight of between about 500 Da and about 1000 Da. In some embodiments, the small molecule has a molecular weight of between about 500 Da and about 2000 Da. In some embodiments, the small molecule has a molecular weight of between about 500 Da and about 5000 Da. The small molecules may be natural or synthesized in the laboratory. In some embodiments, the collection of small molecules may comprise compounds that are structurally related to one another, e.g., are analogs of one another and/or of a common parent compound. In some embodiments, the small molecules screened using the inventive methods may be provided as a combinatorial library prepared by technologies and methods known in the field of combinatorial chemistry. In certain embodiments, the small molecules are non-polymeric, non-oligomeric, and/or non-peptidic. In certain embodiments, the small molecules are drugs, drug-like molecules, or drug candidates.

In certain embodiments, the agent found to bind an exo-site or screened for binding to an exo-site is a polynucleotide or nucleic acid (e.g., DNA, RNA). In certain embodiments, the polynucleotide is a sequence of between 3 and 10 bases, 10 and 20 bases, 20 and 50 bases, or more than 50 bases. In certain embodiments, the agent is a polypeptide. In certain embodiments the agent found to bind an exo-site or screened for binding to an exo-site is a protein (e.g., enzyme, antibody). In certain embodiments, the polypeptide contains between 3 and 10 amino acids, 10 and 20 amino acids, 20 and 50 amino acids, or greater than 50 amino acids. In certain embodiments, the agent found to bind an exo-site or screened for binding to an exo-site is a carbohydrate (e.g., polysaccharide). In certain embodiments, the polysaccharide contains between 3 and 10 monosaccharides, 10 and 20 monosaccharides, 20 and 50 monosaccharides, or greater than 50 monosaccharides.

The library of candidate agents may be made of up of any suitable kind of agent (e.g., small molecule, polynucleotide, polypeptide, protein, carbohydrate). In some embodiments, all candidate agents of a library are the same kind of agent (e.g., all small molecules, all polypeptides). In some embodiments, a library may comprise candidate agents which are different kinds of agents (e.g., small molecules and polypeptides). In some embodiments, the library comprises candidate agents that are based on a similar core or scaffold. In some embodiments, the library comprises candidate agents based on two or more distinct cores or scaffolds.

The library may be of any size suitable for the screening method being employed. In some embodiments, the library has between 2 and 100 members. In some embodiments, the library has between 100 and 1000 members. In some embodiments, the library has between 1000 and 10000 members. In some embodiments, the library has between 10000 and 100000 members. In some embodiments, the library has between 100000 and 1 million members. In some embodiments, the library has between 1 million and 10 million members. In some embodiments, the library has between 10 million and 100 million members. In some embodiments, the library has between 100 million and 1 billion members. In some embodiments, the library has between 1 billion and 10 billion members. In some embodiments, the library has greater than 10 billion members.

The library may be selected based on a known or suspected exo-site binding pocket of a protein. For example, if an exo-site binding molecule for a particular protein exo-site is known the library may comprise candidate agents of a similar kind (e.g., small molecule, polypeptide) or candidate agents based on a similar core or scaffold. The library may also be selected without knowing what type of agents or scaffolds are likely to bind in the exo-site.

The binding of candidate agents to the variants of the protein may be probed by any suitable screening or selection techniques. Screening methods typically involve contacting each candidate agent separately with a target protein, e.g., using a multi-well plate wherein each well is loaded with a different candidate agent. Alternatively selection methods involve contacting all candidate agents of a library with the target protein simultaneously in a one-pot experiment. The time and effort required to test interaction of large libraries with a protein is proportional to the number of library members for screening, but is largely independent of library size for selections. In certain embodiments, the binding of candidate agents to the first and second variant is determined using a screening technique. In some embodiments, the screening technique is a high-throughput screening technique. In certain embodiments, the binding of candidate agents to the first and second variant is determined using a selection technique. Since candidate agents are mixed in one-pot during selection methods, selection techniques require some means of deconvolution the complex mixture, typically by encoding the library members. In certain embodiments, the library is an encoded library. In some embodiments, the library is encoded by attachment of a biopolymer (e.g., nucleic acid, peptide) to candidate agents. Selection or screens may also be run at different concentrations of candidate agents, different concentrations of protein, or different relative concentrations of candidate agents to protein.

In some embodiments, the library is a DNA encoded library. DNA encoded libraries can encode millions of candidate agents with sequence lengths of about 20 nucleotides. Polymerase chain reaction (PCR) methods known in the art allow for the amplification of DNA sequences from minute quantities (e.g., sub-femtomole) of DNA for subsequent sequencing. This may allow for large libraries to be tested for interactions with a protein without synthesis of larger quantities of candidate agents that would be necessary for some activity-based assays (e.g., competitive inhibition of an optically detected probe).

In certain embodiments, a DNA encoded library comprises DNA-encoded candidate agents synthesized by DNA-directed library synthesis. In some embodiments, DNA encoded candidate agents are synthesized by DNA-templated synthesis (DTS). See, e.g., Gartner et al., *Science* (2004), 305:1601-1605; Tse et al., *J. Am. Chem. Soc.* (2008) 130:15611-15626; Brudno et al., *Nat. Chem. Biol.* (2010) 6:148-155; U.S. Patent Application, U.S. Ser. No. 10/101, 030, filed Mar. 19, 2002; and U.S. Patent Application, U.S. Ser. No. 10/643,752, filed Aug. 19, 2003, each of which is incorporated herein by reference. In some embodiments, DNA encoded candidate agents are synthesized using a YoctoReactor system. See e.g., Hansen et al., *J. Am. Chem. Soc.* (2009) 1313:1322-1327, which is incorporated herein by reference. In some embodiments, DNA encoded candidate agents (e.g., polypeptides) are synthesized using a DNA-display. See, e.g., Halpin et al., *PLoS Biol.* (2004), 2:1015-1021; Halpin et al., *PLoS Biol.* (2004) 2:1022-1030; Halpin et al., *PLoS Biol.* (2004) 2:1031-1038, each of which is incorporated herein by reference. In some embodiments, DNA encoded candidate agents (e.g., polypeptides) are synthesized using an encoded self-assembling combinatorial (ESAC) approach. See, e.g., Melkko et al., *Nat. Biotechnol.* (2004) 22:568-574, which is incorporated by reference herein. In some embodiments, DNA encoded candidate agents are synthesized as a DNA-recorded library. See, e.g., Clark et al., *Nat. Chem. Biol.*, 2009, 5:647-654; Buller et al., *Med. Chem. Lett.* (2008) 18:5926-5931; Mannocci et al., *Proc. Natl. Acad. Sci. U.S.A.* (2008) 105:17670-17675, each of which is incorporated herein by reference.

Affinity selections may comprise incubating candidate agents of a library with a variant of a protein with an exo-site. In certain embodiments, the step of contacting comprises incubating a library of candidate agents with each of the first and second variants. In some embodiments, each candidate agent is separately incubated with each of the first and second variants. In some embodiments, the step of screening comprises incubating the encoded candidate agents with each of the first and second variants in parallel. In some embodiments, the step of screening comprises incubating the encoded candidate agents with each of the first and second variants in series. In some embodiments, all of the candidate agents are incubated with each of the first and second variants. In some embodiments, groups of one or more candidate agents are incubated with each of the first and second variants, for example, in the case where not all candidate agents in a library are compatible with each other they may be separated into groups for incubation. The first and second variant may be immobilized on a solid support to facilitate separation of bound molecules of candidate agents from unbound molecules of candidate agents. After incubation the enriched library fraction may be isolated by separation of the proteins attached to a solid support, followed by washing and elution.

For DNA-encoded libraries, identification of the candidate agents following affinity selection may be done using PCR amplification and DNA sequencing. The identified DNA encoded candidate agents may be exposed to DNA primers and then subjected to PCR conditions to amplify the concentration of each codon present following incubation. In some embodiments, the DNA primers are barcoded to identify the specific experiment from which the amplified codons originate. For example, the DNA primers may be encoded to indicate with which variant the candidate agents were incubated (See FIG. 1A), indicate a particular subset from a larger library, or indicate another feature of the particular selection experiment (e.g., agent and/or variant concentration, presence or absence of a substrate or cofactor). In certain embodiments, the candidate agents of a library are incubated with a first variant and second variant; the agents incubated with the first variant are amplified by PCR in the presence of a first set of DNA primers; and the agents incubated with the second variant are amplified by PCR in the presence of a second set of DNA primers.

Sequencing of the candidate agents codons after PCR amplification can be accomplished by any suitable sequencing technology (e.g., Sanger sequencing, microarray hybridization, pyrosequencing, reversible dye-terminator (Solexa) sequencing). See, e.g., Marguiles et al., *Nature* (2005) 437:376-380; Bentley et al., *Nature* (2008) 456:53-59, each of which is incorporated herein by reference. In some embodiments, the amplified DNA codons are sequenced by a high-throughput sequencing method. In some embodiments, the amplified DNA codons are sequenced by pyrosequencing. In some embodiments, the amplified DNA codons are sequenced by reversible dye-terminator (Solexa) sequencing. The sequencing method may provide a sequence abundance or abundance fraction for each candidate agent in the library for which a selection was run. The sequence abundance or abundance fraction for a candidate agent may be calculated by measuring the number of sequence reads corresponding to the individual agent (or agent with a specific primer encoding) and dividing by the measured number of total interpretable sequence reads.

The binding of a candidate agent may be determined as relative binding of a candidate agent compared to other agents in a library. In certain embodiments, the binding is determined by a library binding experiment. In some embodiments, the library binding experiment is an affinity-based selection. In some embodiments, the library binding experiment comprises comparing the abundance of each library member after contacting the library with each protein variant, with a control treatment (e.g., the input preselection library). One or multiple binding experiments may be run in series or in parallel to determine the differential binding between the first and second protein variant.

For DNA encoded libraries, the binding of a candidate agent may be determined as an enrichment factor for the post-selection and pre-selection sequence abundance corresponding to each agent. In some embodiments, the step of determining binding comprises measuring a sequence abundance for the candidate agent codons. In some embodiments, the step of determining binding comprises measuring the relative or absolute library member abundance for the candidate agent DNA coding sequences. In some embodiments, the step of comparing, for each candidate agent, comprises comparing the measured sequence abundance after incubation with the first variant with the measured sequence abundance after incubation with the second variant.

The pre-selection sequence abundance is the sequence abundance measured for a codon corresponding to an individual agent for a sequencing run on the unselected library (e.g., library that has not been incubated with any target). In some embodiments, the unselected library is sequenced multiple times to determine an average background sequence abundance. The post-selection sequence abundance is the sequence abundance measured for a codon corresponding to an individual agent for a sequencing run on the post-selection library (e.g., library that has been incubated with a target and separated to isolate bound agents). The enrichment factor may be calculated by dividing the post-selection sequence abundance by the pre-selection sequence abundance. A significant enrichment factor may indicate that a candidate agent binds to the target protein variant. The binding may be to the exo-site, active site, or another type of protein-agent interaction. In some embodiments, a significant enrichment factor is greater than 1. In some embodiments, a significant enrichment factor is greater than about 2. In some embodiments, a significant enrichment factor is greater than about 3. In some embodiments, a significant enrichment factor is greater than about 4. In some embodiments, a significant enrichment factor is greater than about 5. In some embodiments, a significant enrichment factor is greater than about 10. The significance of enrichment factors may be based not only on the basis of their absolute value, but also by comparison to typical enrichment factor ranges observed for sequences of similar preselection abundance. The measurement of sequence abundance and enrichment factors for analysis of DNA-encoded library selections has also been described in Kleiner et al., *J. Am. Chem. Soc.* (2010) 132:11779-11791; U.S. Patent Application,U.S. Ser. No. 14/130,336, filed Mar. 3, 2014; U.S. patent application Ser. No. 14/786,185, filed Oct. 22, 2015; U.S. patent application Ser. No. 13/812,431, filed Mar. 26, 2013, each of which is incorporated herein by reference.

Figure 1C:
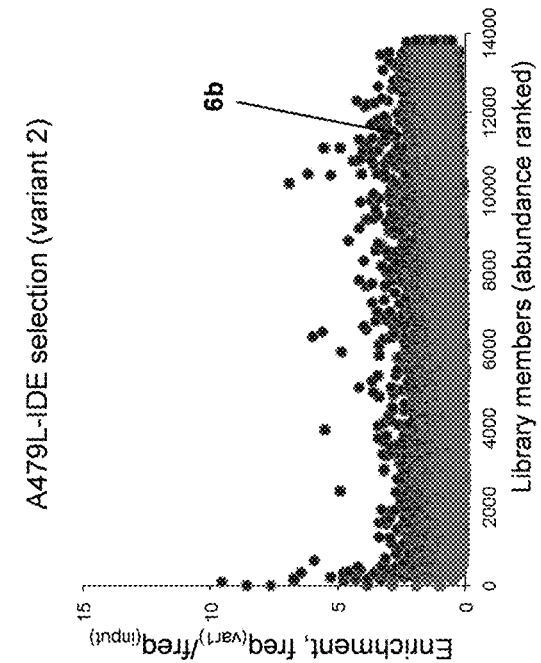
FIG. 1B and FIG. 1C show enrichment results for the strategy in FIG. 1A, which reveal the DNA barcodes that correspond to the building blocks and structures of the IDE exo-site inhibitor 6b ($D_5$-$A_{12}$-$B_8$-$C_6$ barcode, red marker) and other structurally similar hits of the $D_5$-$A_{12}$-$B_8$-Cx barcode family (yellow markers).
Figure 1B:
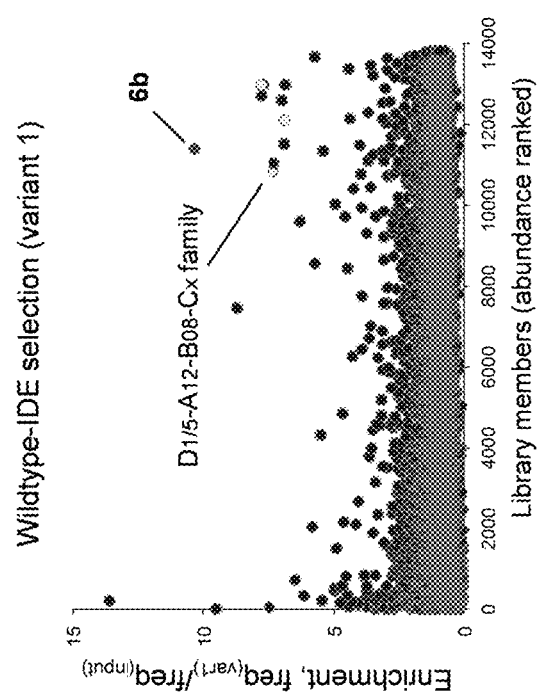

Comparison of binding for a candidate agent to a first protein variant with binding of the candidate agent to a second protein variant can be used to identify the candidate agent as an agent that binds an exo-site of the protein. Candidate agents that have a greater binding to the first variant than the second variant may be exo-site binders. For DNA-encoded libraries, the comparison can be made by using the enrichment factors for each candidate agent. As described above, a significant enrichment factor may indicate that a candidate agent binds to the target protein variant. Differences in the enrichment factor for a selection run with the first variant and a selection run with the second variant indicate that the structural differences between variants have influenced binding of the candidate agent. For example, a candidate agent may have an enrichment factor greater than one with a wild-type protein, but have an enrichment factor less than one or about one for a mutant of the protein with an exo-site "bump," which may mean that the mutation inhibits or interferes with a protein-agent interaction that is present for the wild-type (See FIG. 1B and FIG. 1C). Alternatively, a candidate agent may have similar enrichment factors with both the wild-type and mutant variants, which may indicate that the exo-site is not involved in the protein-agent interaction. The protein variants may also have additional structural differences than just amino acids at the exo-site, thus, in some embodiments, a candidate agent with greater binding to one variant may bind to a non-exo-site position of the protein. In certain embodiments, an agent that binds an exo-site of the protein is identified by determining the binding of the candidate agent is greater for binding to the first variant than binding to the second variant. In certain embodiments, an agent that binds an exo-site of the protein is identified by determining the enrichment factor for the sequence corresponding to the candidate agent is greater for selection with the first variant than selection with the second variant.

Identification of Agents that Bind an Exo-Site of IDE

In certain embodiments, the protein comprising an exo-site is insulin degrading enzyme (IDE). Insulin-degrading enzyme, also referred to as insulysin, insulinase, or insulin protease, is a 110 kDa zinc-binding protease of the M16A metalloprotease subfamily (EC 3.4.24.56). IDE was first identified by its ability to degrade the β chain of insulin and has since been shown to target additional substrates, including, but not limited to, glucagon, amylin, amyloid beta, TGF alpha, beta-endorphin, bradykinin, kallidin, calcitonin-gene related peptide (CGRP), somatostatin, and atrial natriuretic peptide. Non-selective inhibition of IDE may lead to increased levels of both insulin and glucagon, whereas the selective inhibition of IDE to block insulin degradation but allow IDE to continue to catabolize glucagon could enhance insulin concentrations without effecting glucagon concentrations. The agents identified by a method provided herein may be selective or non-selective inhibitors of IDE. In certain embodiments, the selectivity is between insulin and glucagon. In certain embodiments, the selectivity is between insulin and another IDE substrate, between glucagon and another IDE substrate, or between two IDE substrates other than either insulin or glucagon.

Figure 2A:
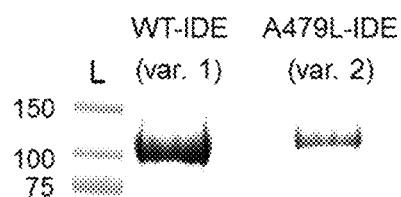
FIG. 2A shows gel electrophoresis of N-His$_6$-WT-IDE (variant 1) and N-His$_6$-A479L-IDE (variant 2) expressed in E. coli and purified using Ni-NTA beads.
Figure 2B:
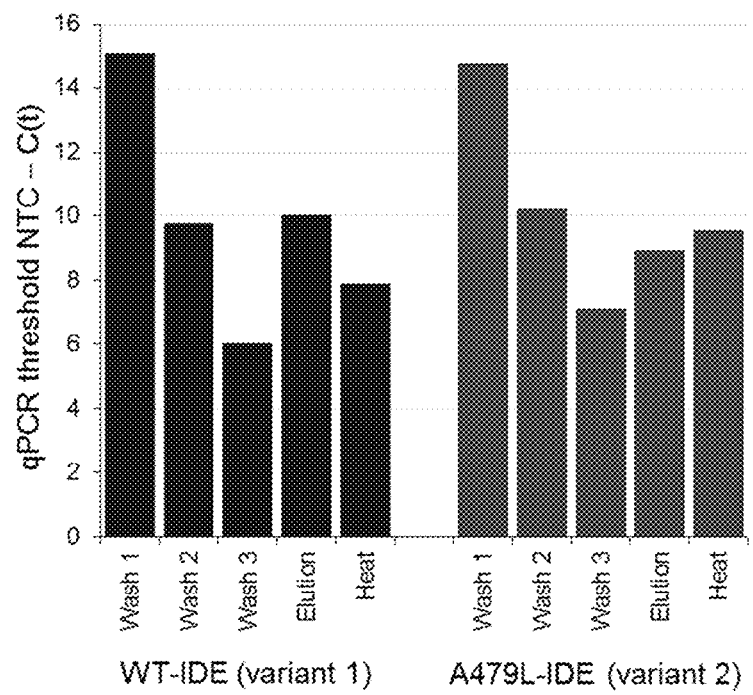
FIG. 2B shows q-PCR monitoring of library abundance following incubation of the DNA-encoded library and variants 1 and 2 in subsequent washings, imidazole elution, and heat elution.
Figure 3:
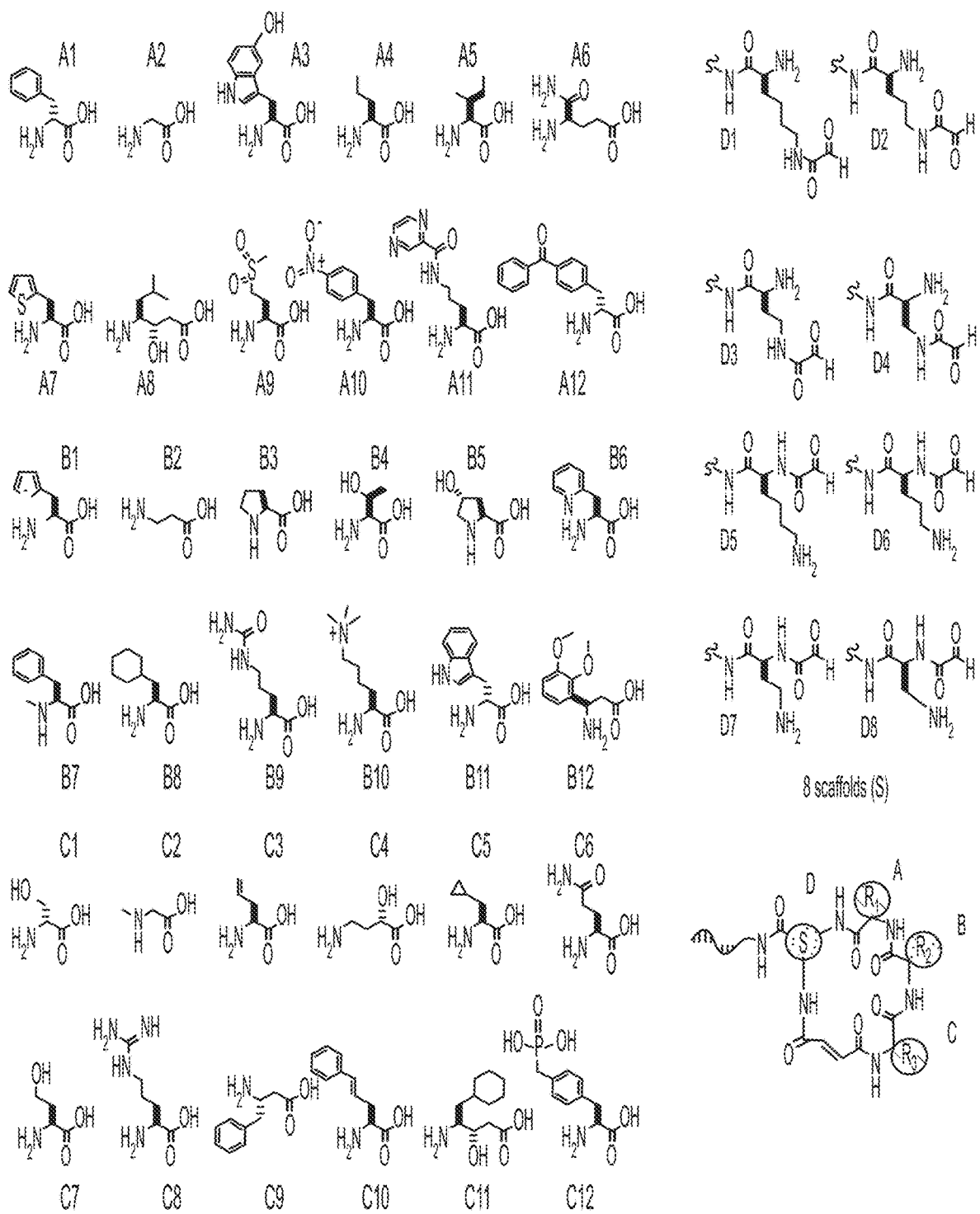
FIG. 3 shows structures of the building blocks comprising the DNA-encoded library used for validation of the in vitro selection method.
Figure 4A:
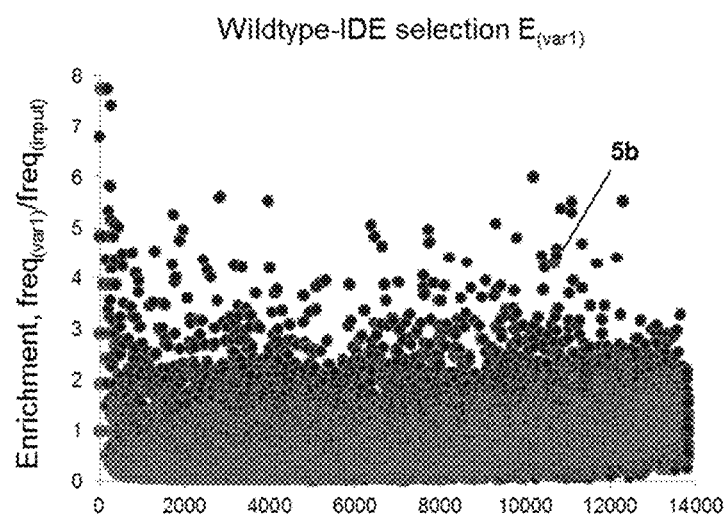
FIG. 4A and FIG. 4B show examples of an in vitro selection of a DNA-encoded library (FIG. 3) displaying enrichment of non-specific binders to wildtype N-His$_6$-IDE (variant 1) and an exo-site "bumped" mutant N-His$_6$-A479L-IDE (variant 2). This library also encodes the known hit 5b highlighted in red, which is not enriched above the noise.
Figure 4B:
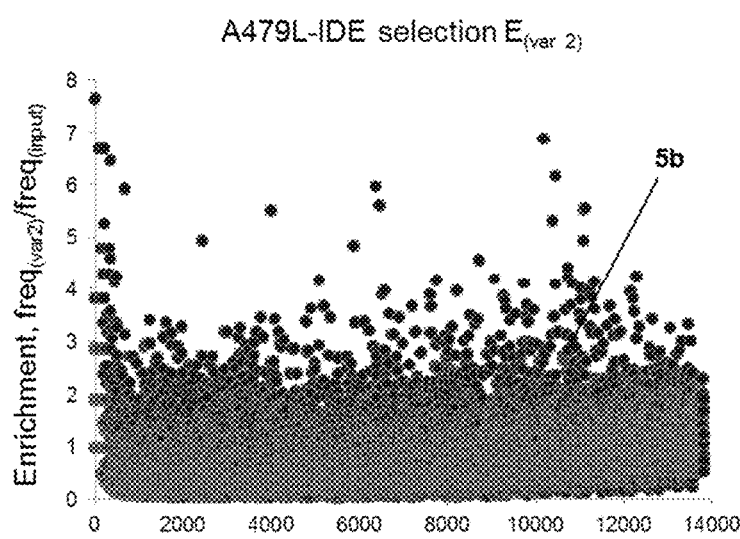
Figure 4C:
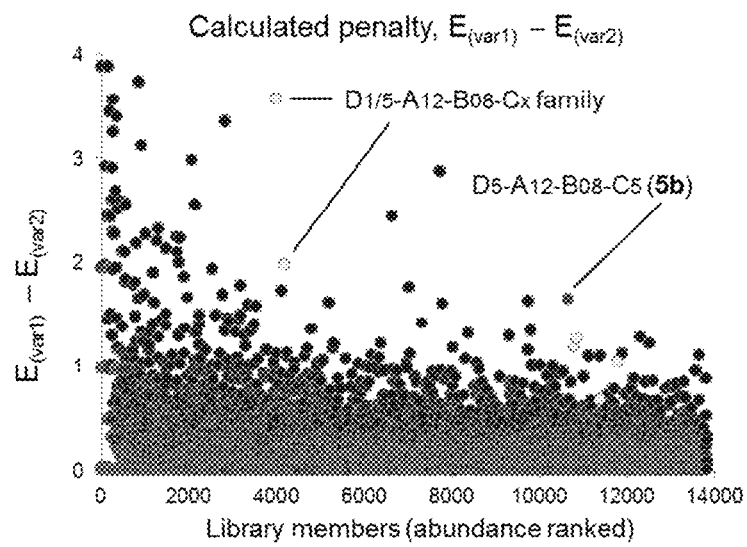
FIG. 4C and FIG. 4D show a demonstration of a mathematical penalty based on the enrichment-parameter against A479L-IDE (variant 2) shown in FIG. 4B applied to the enrichment results of the wildtype IDE (variant 1) selection shown in FIG. 4A. After this calculation the hit 5b appears segregated from other library members because it is a specific exo-site binder of variant 1.
Figure 4D:
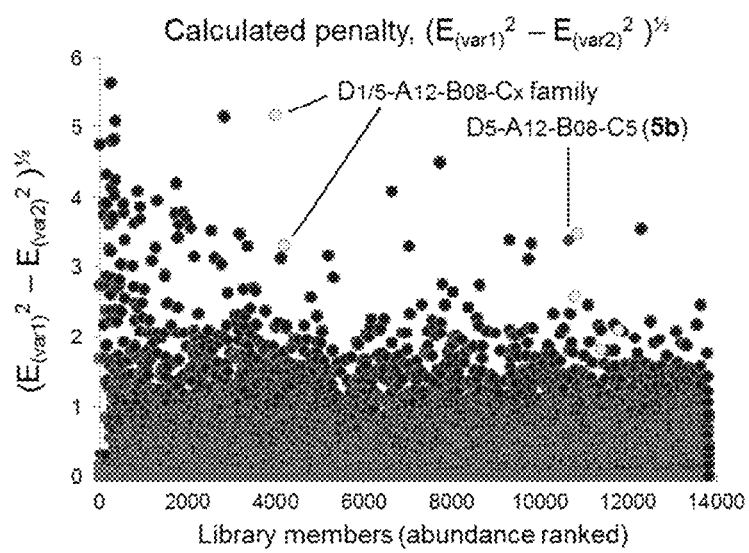
Figure 4E:
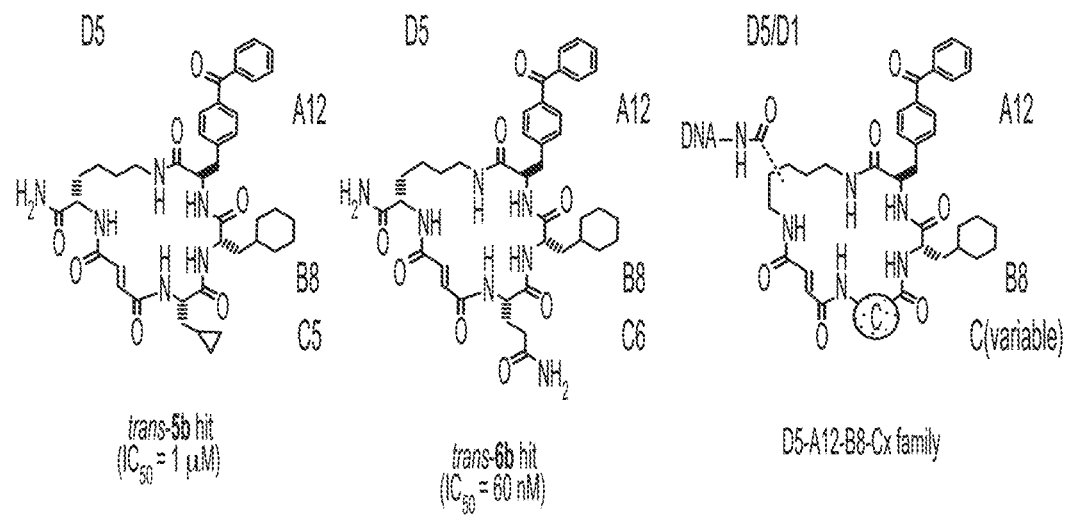
FIG. 4E shows the structure of exo-site IDE inhibitors 5b and 6b from the hit family $D_5$-$A_{12}$-$B_8$-Cx.
Figure 4F:
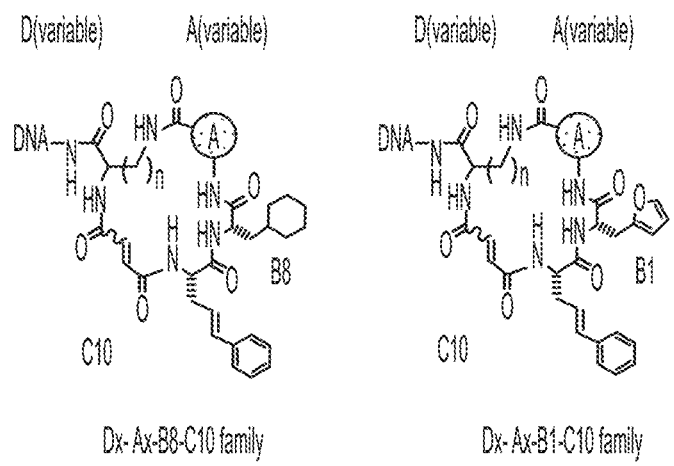
FIG. 4F shows example structures of a family of hits that are non-specific binders of IDE (Dx-Ax-$B_{1/8}$-$C_{10}$).
Figure 5A:
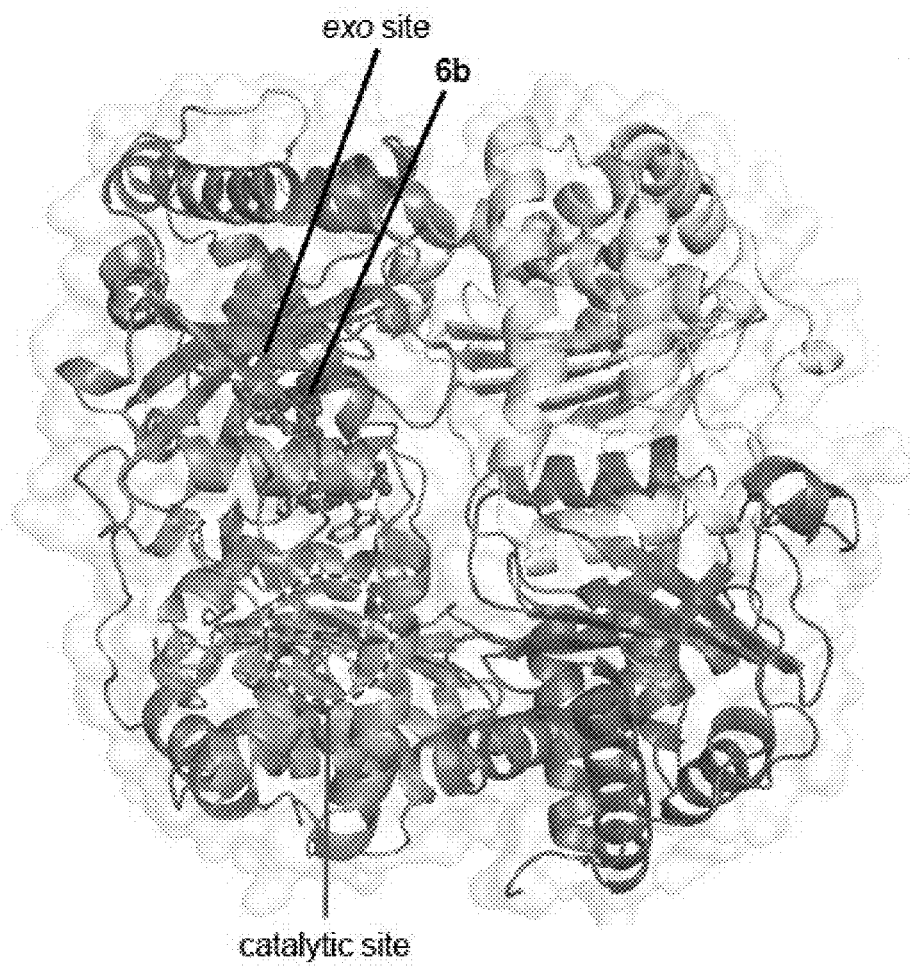
FIGS. 5A-5F show structural data and assay experiments that demonstrate the structural basis for exo-site binding in IDE.
Figure 5B:
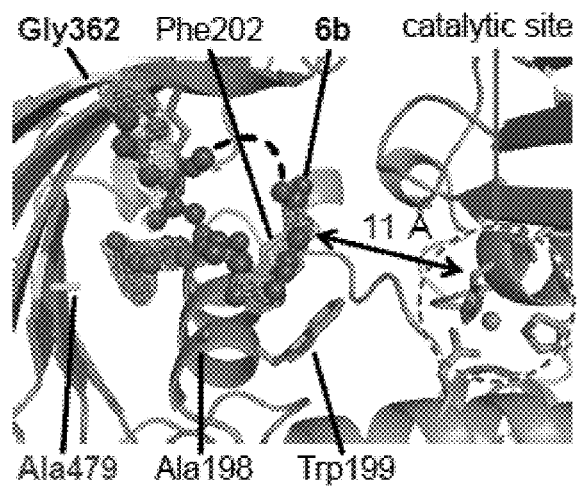
Figure 5C:
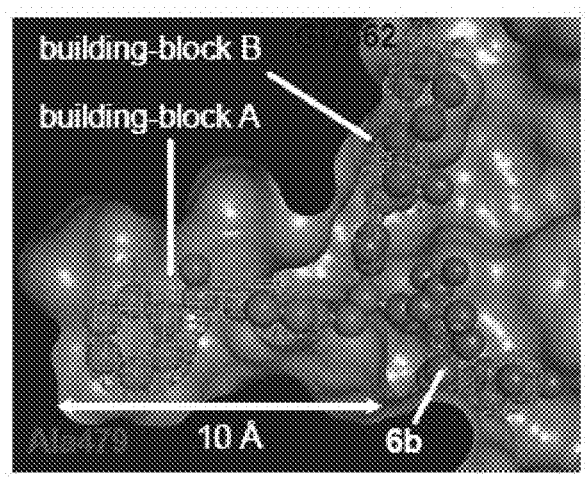
Figure 5D:
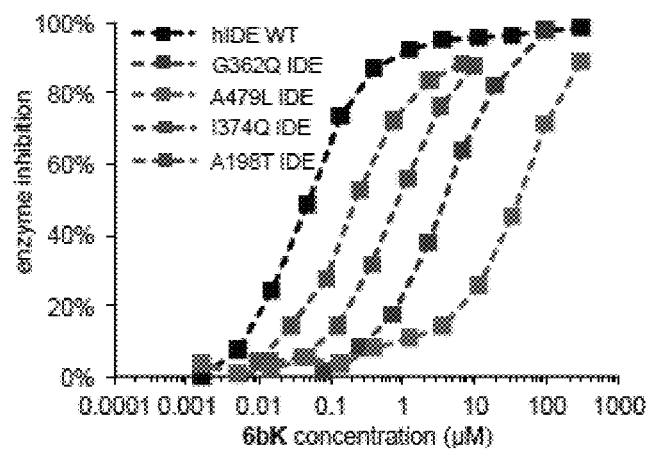
Figure 5E:
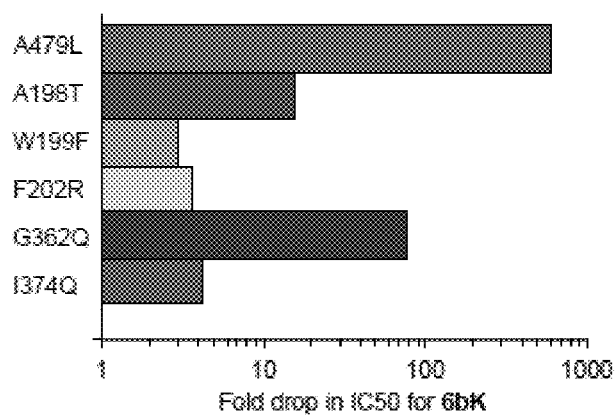
Figure 5F:
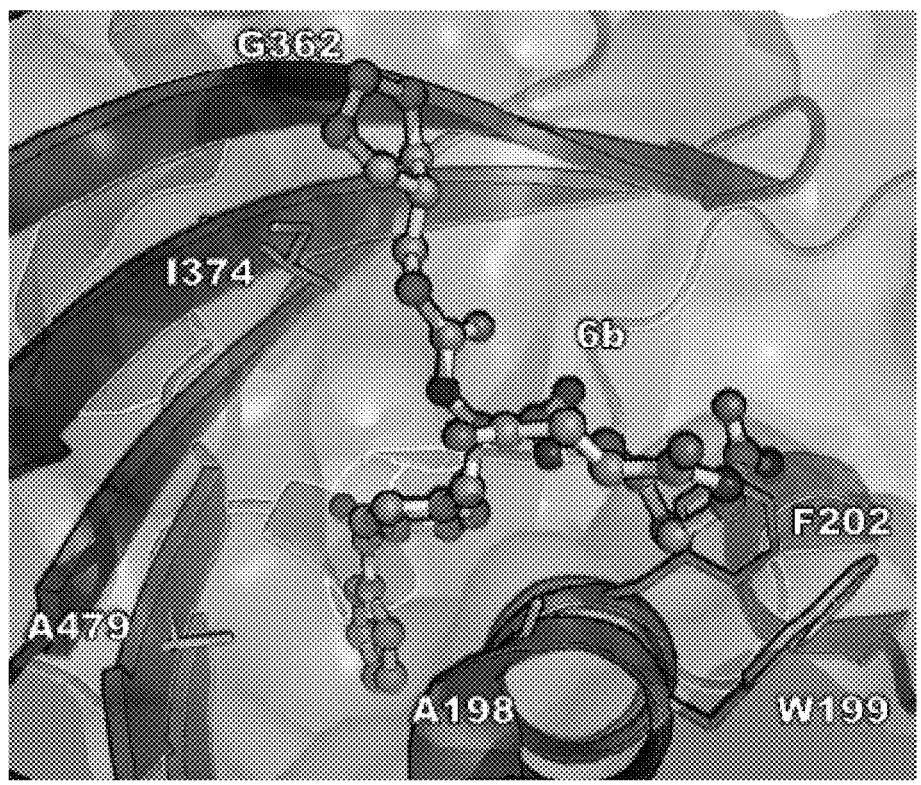

Inhibitors of IDE are described in U.S. Patent Application, U.S. Ser. No. 14/130,336, filed Mar. 3, 2014, which is incorporated herein by reference. IDE has an exo-site or distal binding pocket at the interface of IDE domains 1 and 2. The distal binding pocket comprises a deep hydrophobic pocket about 10 Å in length, defined by the residues Leu201, Glu205, Tyr302, Thr316, and Ala479. (See FIGS. 2A-2C) The binding of selective inhibitors to the distal binding pocket of IDE has been described in Maianti et al., *Nature* (2014), 511, 94-98, which is incorporated herein by reference. The exo-site also comprises a first hydrophobic patch defined by IDE residues Val360, Gly361, Gly362, Lys364, and Ile374, and a second hydrophobic patch defined by IDE residues Ala198, Trp199, and Phe202. An agent identified herein may interact with at least one of the deep hydrophobic pocket, first hydrophobic patch, or second hydrophobic patch. Unless otherwise specified, specific residues of IDE referred to herein are residues in the protein sequence of human insulin-degrading enzyme isoform 1 (see, e.g., SEQ ID NO: 1), though the methods described herein are not limited to human isoform 1 and contemplate using IDE's from other species, other isoforms of IDE, and naturally occurring and synthetic IDE sequence variants and mutations.

In certain embodiments, the first variant of IDE is a wild-type IDE or at least includes a wild type (unmutated) exo-site, and the second variant of IDE is a mutant of IDE. In some embodiments, the mutant is provided by site directed mutagenesis. In some embodiments, the mutation is at a residue of the exo-site (e.g., a residue of the deep hydrophobic pocket, first hydrophobic patch, or second hydrophobic patch). In some embodiments, the mutation is at Ala479, Leu201, Glu205, Tyr302, Thr316, Val360, Gly361, Gly362, Leu364, Ala198, Trp199, Phe202, Tyr314, or Ile374, or is a mutation at a combination of residues thereof. In some embodiments, the mutation is at Leu201, Glu205, Tyr302, Thr316, or Ala479. In some embodiments, the mutation is at Val360, Gly361, Gly362, Lys364, or Ile374. In some embodiments, the mutation is at Ala198, Trp199, and Phe202. In some embodiments, the mutation is A479L, V360Q, G362Q, A198T, W199F, F202R, Y314F, or I374Q, or a combination thereof. In some embodiments, the mutation is A479L.

Pharmaceutical Compositions and Administration

The present disclosure also provides pharmaceutical compositions comprising an agent identified by a method described herein, or a pharmaceutically acceptable salt, solvate, hydrate, polymorph, co-crystal, tautomer, stereoisomer, or prodrug thereof, and optionally a pharmaceutically acceptable excipient. In certain embodiments, the agent described herein is provided in an effective amount in the pharmaceutical composition. In certain embodiments, the effective amount is a therapeutically effective amount. In certain embodiments, the effective amount is a prophylactically effective amount.

In certain embodiments, the effective amount of an agent is an amount effective for treating a metabolic disorder (e.g., diabetes, hyperglycemia, impaired glucose tolerance, insulin resistance, obesity, sodium imbalance, hypertension) in a subject in need thereof. In certain embodiments, the effective amount of an agent is an amount effective for preventing a metabolic disorder (e.g., diabetes, hyperglycemia, impaired glucose tolerance, insulin resistance, obesity, sodium imbalance, hypertension) in a subject in need thereof. In certain embodiments, the effective amount of an agent is an amount effective for reducing the risk of developing a metabolic disorder (e.g., diabetes, hyperglycemia, impaired glucose tolerance, insulin resistance, obesity, sodium imbalance, hypertension) in a subject in need thereof. In certain embodiments, the effective amount of an agent is an amount effective for inhibiting the activity of a protease (e.g., IDE) in a subject or biological sample.

In certain embodiments, the subject being treated is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount of an agent is an amount effective for inhibiting the activity on one or more substrates by a protein by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity on one or more substrates by a protein by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of IDE by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of IDE by not more than about 10%, not more than about 20%, not more than about 30%, not more than about 40%, not more than about 50%, not more than about 60%, not more than about 70%, not more than about 80%, not more than about 90%, not more than about 95%, or not more than about 98%. In certain embodiments, the effective amount is an amount effective for inhibiting the activity of IDE on insulin by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of IDE on insulin by not more than about 10%, not more than about 20%, not more than about 30%, not more than about 40%, not more than about 50%, not more than about 60%, not more than about 70%, not more than about 80%, not more than about 90%, not more than about 95%, or not more than about 98%. In certain embodiments, the effective amount is an amount effective for inhibiting the activity of IDE on glucagon by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of IDE on glucagon by not more than about 10%, not more than about 20%, not more than about 30%, not more than about 40%, not more than about 50%, not more than about 60%, not more than about 70%, not more than about 80%, not more than about 90%, not more than about 95%, or not more than about 98%. In certain embodiments, the effective amount is an amount effective for a range of inhibition between a percentage described in this paragraph and another percentage described in this paragraph, inclusive.

Pharmaceutical compositions described herein can be prepared by any method known in the art of pharmacology. In general, such preparatory methods include bringing the agent described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Agents provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent described herein. In certain embodiments, a dose described herein includes independently between 1 mg and 3 mg, inclusive, of an agent described herein. In certain embodiments, a dose described herein includes independently between 3 mg and 10 mg, inclusive, of an agent described herein. In certain embodiments, a dose described herein includes independently between 10 mg and 30 mg, inclusive, of an agent described herein. In certain embodiments, a dose described herein includes independently between 30 mg and 100 mg, inclusive, of an agent described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

An agent or composition, as described herein, can be administered in combination with one or more additional pharmaceutical agents (e.g., therapeutically and/or prophylactically active agents). The agents or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protease in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including an agent described herein and an additional pharmaceutical agent shows a synergistic effect that is absent in a pharmaceutical composition including one of the agent and the additional pharmaceutical agent, but not both.

Methods of Treatment and Uses

The present disclosure also provides methods that may be useful for the treatment or prevention of a disease, disorder, or condition. In certain embodiments, the disease is associated with a protein comprising an exo-site. In certain embodiments, the disease is associated with reduced expression of a protein comprising an exo-site. In certain embodiments, the disease is associated with elevated expression of a protein comprising an exo-site. In certain embodiments, the disease is associated with ectopic expression of a protein comprising an exo-site. In certain embodiments, the disease is associated with the aberrant activity of a protein comprising an exo-site. In certain embodiments, the disease is associated with the increased activity of a protein comprising an exo-site. In certain embodiments, the disease is associated with the reduced activity of a protein comprising an exo-site. In some embodiments, the disease is associated with the reduced, elevated, or ectopic expression or reduced, elevated, or aberrant activity of a protein comprising an exo-site, wherein the binding of an agent to the exo-site modulates the activity of the protein (e.g., the activity of the protein with respect to a particular substrate). In some embodiments, the disease is associated with the reduced, elevated, or ectopic expression or reduced, elevated, or aberrant activity of a protein comprising an exo-site, wherein the binding of an agent to the exo-site modulates the selectivity of the protein. Aberrant activity refers to activity that is abnormal or undesirable and includes deficient activity of a protein and overactivity of a protein. In some embodiments, deficient activity or overactivity may be caused by reduced, elevated, or ectopic expression of the gene encoding the protein. Aberrant activity may be a pathological level of activity, and may be a cause of a pathological condition or a symptom of a pathological condition. In certain embodiments, the disease is associated with the aberrant selectivity of a protein comprising an exo-site. Aberrant selectivity refers to a protein's selectivity as amongst two or more substrates that is abnormal or undesirable. For example, the protein may have exhibit increased activity toward one substrate versus another, and this activity may be undesired.

In certain embodiments, the protein comprising an exo-site is IDE, and the disease is a metabolic disorder. In certain embodiments, the disorder is a diabetic condition. In certain embodiments, the disorder is diabetes (e.g., type I diabetes mellitus, type II diabetes mellitus, gestational diabetes). In certain embodiments, the disorder is type I diabetes mellitus. In certain embodiments, the disorder is type II diabetes mellitus. In certain embodiments, the disorder is gestational diabetes. In certain embodiments, the disorder is congenital diabetes, cystic-fibrosis-related diabetes, steroid diabetes, or a monogenic diabetes (e.g., mature onset diabetes of the young). In certain embodiments, the disorder is hyperglycemia, impaired glucose tolerance, or insulin resistance. In certain embodiments, the disorder is hypoglycemia or hyperinsulinemia. In certain embodiments, the disorder is an obesity-related condition. In certain embodiments, the disorder is obesity. In certain embodiments, the disorder is class I obesity, class II obesity, class III obesity, or pre-obesity. In certain embodiments, the disorder is undesired weight gain or an over-eating disorder. In some embodiments, the disorder is impaired insulin signaling or insulin resistance. In some embodiments, the disorder is an electrolyte imbalance. In some embodiments, the disorder is sodium imbalance. In some embodiments, the disorder is hypertension.

In certain embodiments, the method of treating a disease comprises administering to a subject in need thereof a therapeutically effective amount of an agent identified by a method described herein, or a pharmaceutically acceptable salt, solvate, hydrate, polymorph, co-crystal, tautomer, stereoisomer, or prodrug thereof. In certain embodiments, the method of treating a disease comprises administering to a subject in need thereof a therapeutically effective amount of an agent identified by a method described herein, or a pharmaceutically acceptable salt thereof. In certain embodiments, the method of treating a disease comprises administering to a subject in need thereof a therapeutically effective amount of a pharmaceutical composition comprising an agent identified by a method described herein, or a pharmaceutically acceptable salt thereof. In certain embodiments, the method of preventing a disease comprises administering to a subject in need thereof a prophylactically effective amount of an agent identified by a method described herein, or a pharmaceutically acceptable salt, solvate, hydrate, polymorph, co-crystal, tautomer, stereoisomer, or prodrug thereof. In certain embodiments, the method of preventing a disease comprises administering to a subject in need thereof a prophylactically effective amount of an agent identified by a method described herein, or a pharmaceutically acceptable salt thereof. In certain embodiments, the method of preventing a disease comprises administering to a subject in need thereof a prophylactically effective amount of a pharmaceutical composition comprising an agent identified by a method described herein, or a pharmaceutically acceptable salt thereof.

The agents identified by a method described herein may exhibit selective inhibition of a protein with an exo-site for modification of one substrate over another substrate. In certain embodiments, the agent identified by a method described herein exhibits selective inhibition of a protein with an exo-site for modification of one or more first substrates over one or more second substrates. Exemplary modifications of a substrate include, but are not limited to, oxidation, reduction, degradation, cleavage, proteolysis, dephosphorylation, phosphorylation, ligation, hydrogenation, dehydrogenation, hydration, dehydration, confirmation change, protein folding, protein aggregation, dimerization, isomerization, and other types of atom or functional group transfer. In certain embodiments, the selectivity for inhibiting modification of one substrate over another is between about 1.1-fold and about 2-fold, between about 2-fold and about 5-fold, between about 5-fold and about 10-fold, between about 10-fold and about 50-fold, between about 50-fold and about 100-fold, or greater than about 100-fold. In certain embodiments, there is no selectivity for one substrate over another substrate.

In certain embodiments, the protein is IDE, and the modification is degradation of an IDE substrate (e.g., insulin, glucagon, amylin, TGF alpha, beta-endorphin, amyloid beta, bradykinin, kallidin, calcitonin-gene related peptide (CGRP), somatostatin, atrial natriuretic peptide). In some embodiments, the first substrate is insulin, and the second substrate is glucagon or amylin. In some embodiments, the first substrate is insulin, and the second substrate is TGF alpha, beta-endorphin, amyloid beta, bradykinin, kallidin, calcitonin-gene related peptide (CGRP), somatostatin, or atrial natriuretic peptide. In some embodiments, the first substrate is glucagon, and the second substrate is insulin or amylin. In some embodiments, the first substrate is glucagon, and the second substrate is TGF alpha, beta-endorphin, amyloid beta, bradykinin, kallidin, calcitonin-gene related peptide (CGRP), somatostatin, or atrial natriuretic peptide. In some embodiments, the first substrate is amylin, and the second substrate is insulin or glucagon. In some embodiments, the first substrate is amylin, and the second substrate is TGF alpha, beta-endorphin, amyloid beta, bradykinin, kallidin, calcitonin-gene related peptide (CGRP), somatostatin, or atrial natriuretic peptide. In some embodiments, the first substrate is TGF alpha, beta-endorphin, amyloid beta, bradykinin, kallidin, calcitonin-gene related peptide (CGRP), somatostatin, or atrial natriuretic peptide, and the second substrate is insulin. In some embodiments, the first substrate is TGF alpha, beta-endorphin, amyloid beta, bradykinin, kallidin, calcitonin-gene related peptide (CGRP), somatostatin, or atrial natriuretic peptide, and the second substrate is glucagon or amylin.

Selectivity of an agent to inhibit modification of specific substrates of a protein with an exo-site may be measured by comparing an assay for modification of a first substrate by the protein in the presence of the agent with an assay for modification of a second substrate by the protein in the presence of the agent.

An agent described herein may interact with a protein with an exo-site to inhibit modification of a first substrate but not modification of a second substrate. The agent may bind near the active site for modification of the first substrate and impede binding of the first substrate but not impede binding of the second substrate or impede binding of the second substrate to a lesser extent. The selectivity of the agent will be particular to the size and shape of the agent, and the location and orientation of binding to the protein exo-site. In some embodiments, the protein is IDE, the first substrate is insulin, and the second substrate is glucagon.

The present disclosure provides methods that may be useful for the treatment of a metabolic disorder by administering an agent identified by a method described herein, or a pharmaceutically acceptable salt, solvate, hydrate, polymorph, co-crystal, tautomer, stereoisomer, or prodrug thereof, or pharmaceutical composition thereof, to a subject in need thereof. In certain embodiments, the agent is administered as a pharmaceutically acceptable salt, stereoisomer, or tautomer thereof. In certain embodiments, the agent is administered as a pharmaceutically acceptable salt of the agent. In certain embodiments, the agent is administered as a specific stereoisomer or mixture of stereoisomers of the agent. In certain embodiments, the agent is administered as a specific tautomer or mixture of tautomers of the agent. In certain embodiments, the agent is administered as a pharmaceutical composition as described herein comprising the agent.

The present disclosure also provides uses of the inventive agents, and pharmaceutically acceptable salts, solvates, hydrates, polymorphs, co-crystals, tautomers, stereoisomers, prodrugs, and pharmaceutical compositions thereof, in the manufacture of medicaments for the treatment or prevention of diseases, disorders, or conditions.

In another aspect, the present disclosure provides methods that may be useful for modulating the activity on one or more substrates by a protein comprising an exo-site in a subject in need thereof, by administering to the subject an agent described herein (e.g., an identified exo-site binding agent), or a pharmaceutically acceptable salt, stereoisomer, or tautomer thereof, or a pharmaceutical composition thereof. In some embodiments, the method is useful for inhibiting the activity of a protein comprising an exo-site. In some embodiments, the method is useful for enhancing the activity of a protein comprising an exo-site.

In another aspect, the present disclosure provides methods that may be useful for modulating the activity on one or more substrates by a protein comprising an exo-site in a biological sample, by contacting the sample with an agent described herein (e.g., an identified exo-site binding agent), or a pharmaceutically acceptable salt, stereoisomer, or tautomer thereof, or a pharmaceutical composition thereof. In some embodiments, the method is useful for inhibiting the activity of a protein comprising an exo-site. In some embodiments, the method is useful for enhancing the activity of a protein comprising an exo-site.

In another aspect, the present disclosure provides methods that may be useful for modulating the substrate selectivity and/or processivity of a protein comprising an exo-site in a subject in need thereof, by administering to the subject an agent described herein (e.g., an identified exo-site binding agent), or a pharmaceutically acceptable salt, stereoisomer, or tautomer thereof, or a pharmaceutical composition thereof. In some embodiments, the method is useful for increasing the selectivity of a protein for modification of a first substrate over modification over a second substrate. In some embodiments, the method is useful for decreasing the selectivity of a protein for modification of a first substrate over modification over a second substrate. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In another aspect, the present disclosure provides methods that may be useful for modulating the substrate selectivity and/or processivity of a protein comprising an exo-site in a biological sample, by contacting the sample with an agent described herein (e.g., an identified exo-site binding agent), or a pharmaceutically acceptable salt, stereoisomer, or tautomer thereof, or a pharmaceutical composition thereof. In some embodiments, the method is useful for increasing the selectivity of a protein for modification of a first substrate over modification over a second substrate. In some embodiments, the method is useful for decreasing the selectivity of a protein for modification of a first substrate over modification over a second substrate. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In another aspect, the present disclosure provides methods that may be useful for modulating the activity of IDE in a subject in need thereof, by administering to the subject an agent described herein (e.g., an identified exo-site binding agent), or a pharmaceutically acceptable salt, stereoisomer, or tautomer thereof, or a pharmaceutical composition thereof. In some embodiments, the method is useful for inhibiting the activity of IDE. In some embodiments, the method is useful for enhancing the activity of IDE.

In another aspect, the present disclosure provides methods that may be useful for modulating the activity of IDE in a biological sample in need thereof, by contacting the sample with an agent described herein (e.g., an identified exo-site binding agent), or a pharmaceutically acceptable salt, stereoisomer, or tautomer thereof, or a pharmaceutical composition thereof. In some embodiments, the method is useful for inhibiting the activity of IDE toward a particular substrate. In some embodiments, the method is useful for enhancing the activity of IDE toward a particular substrate.

In another aspect, the present disclosure provides methods that may be useful for inhibiting the degradation of insulin in a subject in need thereof, by administering to the subject a an agent described herein (e.g., an identified exo-site binding agent), or a pharmaceutically acceptable salt, stereoisomer, or tautomer thereof, or a pharmaceutical composition thereof. In some embodiments, the degradation of insulin is selectively inhibited over the degradation of glucagon. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In another aspect, the present disclosure provides methods that may be useful for inhibiting the degradation of insulin in a biological sample (e.g., cells, tissues, biopsied tissues, purified or partially purified IDE), by contacting the sample with an agent described herein (e.g., an identified exo-site binding agent), or a pharmaceutically acceptable salt, stereoisomer, or tautomer thereof, or a pharmaceutical composition thereof. In some embodiments, the degradation of insulin is selectively inhibited over the degradation of glucagon. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Definitions

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the agents of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the agent, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The agents described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to an agent that is associated with water. Typically, the number of the water molecules contained in a hydrate of an agent is in a definite ratio to the number of the agent molecules in the hydrate. Therefore, a hydrate of an agent may be represented, for example, by the general formula R.x $H_2O$, wherein R is the agent, and x is a number greater than 0. A given an agent may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible agents or compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that agents or compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When an agent or compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral agent or compound can exist as either individual enantiomer or as a mixture thereof. A mixture containing equal proportions of the enantiomers is called a "racemic mixture".

The term "polymorph" refers to a crystalline form of an agent (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of an agent can be prepared by crystallization under different conditions.

The term "co-crystal" refers to a crystalline structure composed of at least two components. In certain embodiments, a co-crystal contains an agent of the present disclosure and one or more other component, including but not limited to, atoms, ions, molecules, or solvent molecules. In certain embodiments, a co-crystal contains an agent of the present disclosure and one or more solvent molecules. In certain embodiments, a co-crystal contains an agent of the present disclosure and one or more acid or base. In certain embodiments, a co-crystal contains an agent of the present disclosure and one or more components related to said agent, including not limited to, an isomer, tautomer, salt, solvate, hydrate, synthetic precursor, synthetic derivative, fragment or impurity of said agent.

The term "prodrug" refers to agents or compounds that have cleavable groups and become by solvolysis or under physiological conditions the agents described herein, which are pharmaceutically active in vivo. Such examples include, but are not limited to, choline ester derivatives and the like, N-alkylmorpholine esters and the like. Other derivatives of the agents described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid agent or compound with a substituted or unsubstituted amine, or acid anhydrides, or mixed anhydrides. Simple aliphatic or aromatic esters, amides, and anhydrides derived from acidic groups pendant on the agents or compounds described herein are particular prodrugs. In some cases it is desirable to prepare double ester type prodrugs such as (acyloxy)alkyl esters or ((alkoxycarbonyl)oxy)alkylesters. C1-C8 alkyl, C2-C8 alkenyl, C2-C8 alkynyl, aryl, C7-C12 substituted aryl, and C7-C12 arylalkyl esters of the agents or compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing an agent described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

As used herein the term "inhibit" or "inhibition" in the context of proteins, for example, in the context of IDE, refers to a reduction in the activity of the protein. In some embodiments, the term refers to a reduction of the level of protein activity, e.g., IDE activity, to a level that is statistically significantly lower than an initial level, which may, for example, be a baseline level of protein activity. In some embodiments, the term refers to a reduction of the level of protein activity, e.g., IDE activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of protein activity.

As used herein, the term "insulin degrading enzyme" or "IDE" refers to the enzyme primarily responsible for insulin catabolism in vivo which is also referred to as insulysin, insulinase, or insulin protease. IDE is a 110 kDa zinc-binding protease of the M16A metalloprotease subfamily (EC 3.4.24.56), which degrades the beta chain of insulin and is also known to process additional substrates including, but not limited to, glucagon, amylin, amyloid TGF alpha, beta-endorphin, amyloid beta, bradykinin, kallidin, calcitonin-gene related peptide (CGRP), somatostatin, and atrial natriuretic peptide. IDE enzymes (also referred to herein as IDE proteins) and their respective encoding RNA and DNA sequences according to some aspects of this disclosure include human IDE protein and encoding sequences, as well as, in some embodiments, IDE proteins and encoding sequences from other species, for example, from other mammals (e.g., IDE proteins and encoding sequences from mouse, rat, cat, dog, cattle, goat, sheep, pig, or primate), from other vertebrates, and from insects. In some embodiments, an IDE inhibitor provided herein is specific for an IDE from a species, e.g., for human IDE, mouse IDE, rat IDE, and so on. In some embodiment, an IDE provided herein inhibits IDEs from more than one species, e.g., human IDE and mouse IDE. In some embodiments, an IDE provided herein exhibits equipotent inhibition of IDEs from more than one species, e.g., equipotent inhibition of human and mouse IDEs. The term IDE further includes, in some embodiments, sequence variants and mutations (e.g., naturally occurring or synthetic IDE sequence variants or mutations), and different IDE isoforms. In some embodiments, the term IDE includes protein or encoding sequences that are homologous to an IDE protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with an IDE sequence, for example, with an IDE sequence provided herein. In some embodiments, the term IDE refers to a protein exhibiting IDE activity, for example, a protein exhibiting insulin-targeted protease activity, or a nucleic acid sequence encoding such a protein. In some embodiments, the term IDE included proteins that exhibit at least 50%, at least 60%, at least 70%, at least 80%, at least 90%, at least 95%, or at least 100% insulin-targeting protease activity as compared to a known IDE protein or encoding sequence, for example, as compared to an IDE sequence provided herein. IDE protein and encoding gene sequences are well known to those of skill in the art, and exemplary protein sequences include, but are not limited to, the following sequences. Additional IDE sequences will be apparent to those of skill in the art, and the disclosure is not limited to the exemplary sequences provided herein.

>gi|155969707|ref|NP_004960.2| insulin-degrading enzyme isoform 1 [Homo sapiens]
(SEQ ID NO: 1)
MRYRLAWLLHPALPSTFRSVLGARLPPPERLCGFQKKTYSKMNNPAIKRI

GNHITKSPEDKREYRGLELANGIKVLLISDPTTDKSSAALDVHIGSLSDP

PNIAGLSHFCEHMLFLGTKKYPKENEYSQFLSEHAGSSNAFTSGEHTNYY

FDVSHEHLEGALDRFAQFFLCPLFDESCKDREVNAVDSEHEKNVMNDAWR

LFQLEKATGNPKHPFSKFGTGNKYTLETRPNQEGIDVRQELLKFHSAYYS

SNLMAVCVLGRESLDDLTNLVVKLFSEVENKNVPLPEFPEHPFQEEHLKQ

LYKIVPIKDIRNLYVTFPIPDLQKYYKSNPGHYLGHLIGHEGPGSLLSEL

KSKGWVNTLVGGQKEGARGEMFFIINVDLTEEGLLHVEDIILHMFQYIQK

LRAEGPQEWVFQECKDLNAVAFREKDKERPRGYISKIAGILHYYPLEEVL

TAEYLLEEFRPDLIEMVLDKLRPENVRVAIVSKSFEGKTDRTEEWYGTQY

KQEAIPDEVIKKWQNADLNGKFKLPTKNEFIPINFEILPLEKEATPYPAL

IKDTAMSKLWFKQDDKFFLPKACLNFEFFSPFAYVDPLHCNMAYLYLELL

KDSLNEYAYAAELAGLSYDLQNTIYGMYLSVKGYNDKQPILLKKIIEKMA

TFEIDEKRFEIIKEAYMRSLNNFRAEQPHQHAMYYLRLLMTEVAWTKDEL

KEALDDVILPRLKAFIPQLLSRLHIEALLHGNITKQAALGIMQMVEDTLI

EHAHTKPLLPSQLVRYREVQLPDRGWEVYQQRNEVHNNCGIEIYYQTDMQ

STSENMFLELFCQIISEPCFNTLRIKEQLGYIVESGPRRANGIQGLRFII

QSEKPPHYLESRVEAFLITMEKSIEDMTEEAFQKHIQALAIRRLDKPKKL

SAECAKYWGEIISQQYNFDRDNTEVAYLKTLIKEDIIKFYKEMLAVDAPR

RHKVSVHVLAREMDSCPVVGEFPCQNDINLSQAPALPQPEVIQNMTEFKR

GLPLFPLVKPHINFMAAKL

>gi|260099676|ref|NP_001159418.1| insulin-degrading enzyme isoform 2 [Homo sapiens]
(SEQ ID NO: 2)
MSKLWFKQDDKFFLPKACLNFEFFSPFAYVDPLHCNMAYLYLELLKDSLN -continued
EYAYAAELAGLSYDLQNTIYGMYLSVKGYNDKQPILLKKIIEKMATFEID

EKRFEIIKEAYMRSLNNFRAEQPHQHAMYYLRLLMTEVAWIKDELKEALD

DVILPRLKAFIPQLLSRLHIEALLHGNITKQAALGIMQMVEDTLIEHAHT

KPLLPSQLVRYREVQLPDRGWFVYQQRNEVHNNCGIEIYYQTDMQSTSEN

MFLELFCQIISEPCFNTLRIKEQLGYIVFSGPRRANGIQGLRFIIQSEKP

PHYLESRVEAFLITMEKSIEDMTEEAFQKHIQALAIRRLDKPKKLSAECA

KYWGEIISQQYNFDRDNIEVAYLKTLIKEDIIKFYKEMLAVDAPRRHKVS

VHVLAREMDSCPVVGEFPCQNDINLSQAPALPQPEVIQNMTEFKRGLPLF

PLVKPHINFMAAKL

>gi|121583922|ref|NP_112419.2| insulin-degrading
enzyme [Mus musculus]
(SEQ ID NO: 3)
MRNGLVWLLHPALPGILRSILGARPPPAKRLCGFPKQTYSTMSNPAIQRI

EDQIVKSPEDKREYRGLELANGIKVLLISDPITDKSSAALDVHIGSLSDP

PNIPGLSHFCEHMLFLGIKKYPKENEYSQFLSEHAGSSNAFTSGEHTNYY

FDVSHEHLEGALDRFAQFFLCPLFDASCKDREVNAVDSEHEKNVMNDAWR

LFQLEKAIGNPKHPFSKFGIGNKYTLETRPNQEGIDVREELLKFHSTYYS

SNLMAICVLGRESLDDLINLVVKLFSEVENKNVPLPEFPEHPFQEEHLRQ

LYKIVPIKDIRNLYVTFPIPDLQQYYKSNPGHYLGHLIGHEGPGSLLSEL

KSKGWVNTLVGGQKEGARGEMFFIINVDLTEEGLLHVEDIILHMFQYIQK

LRAEGPQEWVFQECKDLNAVAFREKDKERPRGYISKIAGKLHYYPLNGVL

TAEYLLEEFRPDLIDMVLDKLRPENVRVAIVSKSFEGKTDRIEQWYGTQY

KQEAIPEDIIQKWQNADLNGKFKLPTKNEFIPINFEILSLEKDATPYPAL

IKDTAMSKLWFKQDDKFFLPKACLNFEFFSPFAYVDPLHCNMAYLYLELL

KDSLNEYAYAAELAGLSYDLQNTIYGMYLSVKGYNDKQPILLKKITEKMA

TFEIDKKRFEIIKEAYMRSLNNFRAEQPHQHAMYYLRLLMTEVAWTKDEL

KEALDDVILPRLKAFIPQLLSRLHIEALLHGNITKQAALGVMQMVEDTLI

EHAHTKPLLPSQLVRYREVQLPDRGWEVYQQRNEVHNNCGIEIYYQTDMQ

STSENMFLELFCQIISEPCFNTLRIKEQLGYIVESGPRRANGIQGLRFII

QSEKPPHYLESRVEAFLITMEKAIEDMTEEAFQKHIQALAIRRLDKPKKL

SAECAKYWGEIISQQYNYDRDNIEVAYLKTLIKDDIIRFYQEMLAVDAPR

RHKVSVHVLAREMDSCPVVGEFPSQNDINLSEAPPLPQPEVIHNMTEFKR

GLPLFPLVKPHINFMAAKL

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an α anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

The term "distal binding pocket" refers to a substrate binding pocket distinct from the active site of an enzyme. The distal binding pocket may be at least about 2 angstroms, at least about 3 angstroms, at least about 5 angstroms, at least about 10 angstroms, at least about 15 angstroms, at least about 20 angstroms, at least about 25 angstroms, at least about 30 angstroms, at least about 35 angstroms, at least about 40 angstroms, at least about 45 angstroms, at least about 50 angstroms, at least about 55 angstroms, at least about 60 angstroms, at least about 65 angstroms, at least about 70 angstroms, at least about 75 angstroms, at least about 80 angstroms, at least about 85 angstroms, at least about 90 angstroms, at least about 95 angstroms, or at least about 100 angstroms from the active site of the enzyme.

The term "exo-site" is a secondary binding site, remote from the active site, on a protein, such as an enzyme. It may be characterized by any of the embodiments described herein. The exo-site may be at least about 2 angstroms, at least about 3 angstroms, at least about 5 angstroms, at least about 10 angstroms, at least about 15 angstroms, at least about 20 angstroms, at least about 25 angstroms, at least about 30 angstroms, at least about 35 angstroms, at least about 40 angstroms, at least about 45 angstroms, at least about 50 angstroms, at least about 55 angstroms, at least about 60 angstroms, at least about 65 angstroms, at least about 70 angstroms, at least about 75 angstroms, at least about 80 angstroms, at least about 85 angstroms, at least about 90 angstroms, at least about 95 angstroms, or at least about 100 angstroms from the active site of the enzyme.

The term "allosteric site" refers to a binding site on a protein that is distinct from the active site and binds a substrate molecule that regulates the enzyme. Allosteric sites allow substrates to bind to the protein, often resulting in a conformational change involving protein dynamics. Substrates that enhance the protein's activity are referred to as allosteric activators, whereas those that decrease the protein's activity are called allosteric inhibitors. The distal binding pocket may be at least about 2 angstroms, at least about 3 angstroms, at least about 5 angstroms, at least about 10 angstroms, at least about 15 angstroms, at least about 20 angstroms, at least about 25 angstroms, at least about 30 angstroms, at least about 35 angstroms, at least about 40 angstroms, at least about 45 angstroms, at least about 50 angstroms, at least about 55 angstroms, at least about 60 angstroms, at least about 65 angstroms, at least about 70 angstroms, at least about 75 angstroms, at least about 80 angstroms, at least about 85 angstroms, at least about 90 angstroms, at least about 95 angstroms, or at least about 100 angstroms from the active site of the enzyme.

The term "isoform" refers to protein isoforms or protein variants, describing either several different forms of protein coded from the same gene, or proteins with amino acid sequence and functional similarities, even when they are products of different genes.

The term "active site" is the region of an enzyme where substrate molecules bind and undergo a chemical reaction. The active site comprises residues that form temporary bonds with the substrate, known as the "binding site," and residues that catalyze a reaction of that substrate, known as the "catalytic site."

The term "substrate" or "enzyme substrate" refers to a molecule upon which an enzyme acts. Enzymes catalyze chemical reactions involving the substrate(s). In some embodiments, a substrate may bind to the active site and be subsequently transformed into one or more products followed by release from the active site. In some embodiments, a substrate may be unchanged after binding to an enzyme. In some embodiments, a substrate may bind to an exo-site of an enzyme, as defined herein.

EXAMPLES

In order that the invention described herein may be more fully understood, the following examples are set forth. The examples described in this application are offered to illustrate the agents, pharmaceutical compositions, and methods provided herein and are not to be construed in any way as limiting their scope.

Dual In Vitro Selection of a DNA-Encoded Library with Immobilized Wildtype Enzyme and Exo-Site Mutant Site-Directed Mutagenesis, Expression, and Purification of Human Wildtype IDE and IDE-A479L Exo-Site Mutant.

The reported N-His$_6$-tagged human IDE$_{42-1019}$ construct (isoform containing the amino acids 42-1019 of the IDE sequence) was introduced in the expression plasmid pTrcHis-A (Invitrogen) using primers for uracil-specific excision reactions (USER) by Taq (NEB) and Pfu polymerases (PfuTurbo CX®, Agilent). The IDE gene was amplified with the primers (SEQ ID NO: 4)
5'-<u>ATCATCATATGAATAATCCAGCCA-*dU*</u>-CAAGAGAATAGG
and (SEQ ID NO: 5)
5'-<u>ATGCTAGCCATACCTCAGAG-*dU*</u>-*TTTGCAGCCATGAAG*
(underlined sequences represent overhangs, and italics highlight the PCR priming sequence).

Similarly, the pTrcHis-A vector was amplified for USER cloning with the primers (SEQ ID NO: 6)
5'-<u>ATGGCTGGATTATTCATATGATGA-*dU*</u>-*GATGATGATGAGAACCC*
and (SEQ ID NO: 7)
5'-<u>ACTCTGA*GGTATGGCTAGCA-*dU*</u>-*GACTGGTG*.

The IDE-A479L mutation was introduced by amplifying the wild-type IDE pTrcHis-A vector construct with USER cloning primers carrying the mutation in the overhang region:

(SEQ ID NO: 8)
5'-<u>ATGTCCGGGTTCTGATAGTTTCTAAA-dU</u>-CTTTTGAAGGAAAAACTG
and (SEQ ID NO: 9)
5'-<u>ATTTAGAAACTATCAGAACCCGGACA-dU</u>-TTTCTGGTCTGAG.

All PCR products were purified on microcentrifuge membrane columns (MinElute®, Qiagen) and quantified by UV absorbance (NanoDrop). Each fragment (0.2 pmol) was combined in a 10 μL reaction mixture containing 20 units DpnI (NEB), 0.75 units of USER mix (Endonuclease VIII and Uracil-DNA Glycosylase, NEB), 20 mM Tris-acetate, 50 mM potassium acetate, 10 mM magnesium acetate, 1 mM dithiothreitol at pH 7.9 (1×NEBuffer 4). The reactions were incubated at 37° C. for 45 min, followed by heating to 80° C. and slow cooling to 30° C. (0.2° C./s). The hybridized constructs were directly used for heat-shock transformation of chemically competent NEB turbo *E. coli* cells according to the manufacturer's instructions. Transformants were selected on carbenicillin LB agar, and isolated colonies were cultured overnight in 2 mL LB.

The plasmids were extracted using microcentrifuge membrane column kits (Miniprep®, Qiagen), and the sequence of genes and vector junctions were confirmed by Sanger sequencing. The plasmid constructs were transformed by heat-shock into chemically-competent expression strain Rosetta 2 (DE3) pLysS *E. coli* cells (EMD Millipore), and selected on carbenicillin/chloramphenicol LB agar. Cells transformed with IDE pTrcHis A constructs were cultured overnight at 37° C. in 2 XYT media (31 g in 1 L) containing 100 μg/mL ampicillin and 34 μg/mL chloramphenicol. Expression of His6-tagged IDE proteins was induced when the culture measured OD600 ~0.6 by addition of isopropyl-β-D-1-thiogalactopyranoside (IPTG) to 1 mM final concentration, incubated overnight at 37° C., followed by centrifugation at 10,000 g for 30 min at 4° C.

Recombinant His6-tagged IDE and IDE-A479L were purified by Ni(II)-affinity chromatography (IMAC sepharose beads, GE Healthcare®) according to the manufacturer's instructions. The cell pellets were resuspended in pH 8.0 buffer containing 50 mM phosphate, 300 mM NaCl, 10 mM imidazole, 1% Triton X-100 and 1 mM tris(2-carboxyethyl) phosphine hydrochloride (TCEP), and were lysed by probe sonication for 4 min at <4° C., followed by clearing of cell debris by centrifugation at 10,000 g for 25 min at 4° C. The supernatant was incubated with Ni(II)-doped IMAC resin (2 mL) for 3 h at 4° C. The resin was washed twice with the cell resuspension/lysis buffer, and three times with pH 8.0 buffer containing 50 mM phosphate, 300 mM NaCl, 50 mM imidazole and 1 mM TCEP. Elution was performed in 2 mL aliquots by raising the imidazole concentration to 250 mM and subsequently to 500 mM in the previous buffer. The fractions were combined and the buffer was exchanged to the recommended IDE buffer (R&D) using spin columns with 100 KDa molecular weight cut off membranes (Millipore). Protein yields were typically ~10 μg/L, and >90% purity based on gel electrophoresis analysis (Coomassie stained). IDE-specific protease activity was >95% as assessed by inhibition of degradation of peptide substrate Mca-RPPGFSAFK(Dnp)-OH (R&D) by inhibitor 6bK (20 μM final), and compared with pre-quantitated commercially available human IDE (R&D).

Dual In Vitro Selection of a DNA-Templated Library with Immobilized Human IDE and IDE-A479L Exo-Site Mutant.

Recombinant N-His$_6$-tagged human IDE$_{42-1019}$ and A479L-IDE$_{42-1019}$ (~10 μg) were immobilized on cobalt magnetic beads (Dynabeads® His-Tag Isolation & Pull-down, Invitrogen®) by incubating the protein solutions with beads (30 μL) at 4° C. for 30 min in 300 μL of pH 8.0 buffer containing 50 mM phosphate, 300 mM NaCl and 0.01% Tween-20 (PBST buffer), and washed twice with the same buffer. The two individually prepared protein-bead suspensions were incubated for 30 min with 5 pmol of the Liu lab 13,824-membered DNA-templated macrocycle library[1] at 4° C., in pH 7.4 buffer containing 50 mM Tris-HCl, 150 mM NaCl, 0.05% Tween-20 (TBST buffer) supplemented with 0.01% BSA and 3 mg/mL yeast RNA (Ambion®). The beads were washed three times with 200 μL TBST buffer. The enriched library fraction was eluted by treatment with 200 mM imidazole in PBST buffer (50 μL) for 5 min.

PCR amplification of the enriched pool of library barcodes, and input library, was performed in two steps. The first amplification used a set of primers differentiated by addition of extra bases as a diversity element ($N_{0-5}$) for sequencing purposes, and secondly using primers that append adaptors for Illumina sequencing and a 7-base identifier (XXXXXX). The first set of primers were 5'-ACACTCTTTCCCTACACGACGCTCTTCCGATCT ($N_{0-5}$)GAGTGGGATG (SEQ ID NO: 10) and TGGAGTCAGACGTGTGCTCTTCCGATCTCCCTGTACAC (SEQ ID NO: 11). The adaptor primers were 5'-CAAGCAGAAGACGGCATACGAGATXXXXXXXGTGACTGGAGTTCAGACGTGTGC TCTTC (SEQ ID NO: 12) and 5'-AATGATACGGCGACCACCGAGATCTACACXXXXXXX ACACTCTTTCCCTACACGAC (SEQ ID NO: 13). The PCR amplicons were purified by polyacrylamide gel electrophoresis, extracted, and quantified using UV absorbance (NanoDrop) and qPCR (KAPA Biosystems).

High-throughput DNA sequencing was performed on an Illumina MiSeq instrument to yield an average of ~1 million sequence reads for each selection, untreated bead control and pre-selection library. Deconvolution of library barcodes and enrichment calculations were performed with custom software as described previously.[1] Variations in library member abundance as a result of binding to immobilized IDE was revealed by calculating fold-enrichment over the pre-selection library for the two independent selection experiments.

REFERENCES

1. Kleiner, R. E., Dumelin, C. E., Tiu, G. C., Sakurai, K. & Liu, D. R. In vitro selection of a DNA-templated small-molecule library reveals a class of macrocyclic kinase inhibitors. *J. Am. Chem. Soc.*(2010) 132, 11779-11791.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of identifying a small molecule that binds an exo-site of a protein, the method comprising:
providing a first variant of the protein, wherein the protein comprises an exo-site;
providing a second variant of the protein, wherein the exo-site of the second variant comprises at least one different amino acid than the exo-site of the first variant;
contacting each member of a library of small molecules with each of the first and second variants;
determining an enrichment-based parameter for each small molecule with respect to each of the first and second variants by a binding assay;
comparing, for each small molecule, the binding to the first variant with the binding to the second variant, wherein if the enrichment-based parameter using the first protein variant is greater than the enrichment-based parameter using the second protein variant, then the small molecule is identified as an agent that binds an exo-site of the protein;
wherein the exo-site is not an allosteric site; wherein the library is an encoded library; and
wherein when a small molecule binds to the exo-site, the bound exo-site modulates substrate selectivity or binding preferences of an active site of the protein but does not change the catalytic activity of the active site of the protein.

2. The method of claim 1, wherein the bound exo-site does not induce a conformational change in the active site of the protein.

3. The method of claim 1, wherein the exo-site comprises a binding pocket defined by amino acids that are distinct from the amino acids of the active site of the protein.

4. The method of claim 1, wherein the first variant is a wild-type protein or a truncated domain of a wild-type protein.

5. The method of claim 1, wherein the second variant comprises a mutant of the first variant, wherein one amino acid of the exo-site in the first variant is replaced with a different amino acid in the second variant.

6. The method of claim 5, wherein the replacement amino acid in the second variant comprises a side chain with a higher number of non-hydrogen atoms than the replaced amino acid in the first variant.

7. The method of claim 1, wherein the first and second variants are two different isoforms of the protein, or truncated domains from two different isoforms.

8. The method of claim 1, wherein the step of contacting comprises incubating each of the encoded small molecules with each of the first and second variants in parallel.

9. The method of claim 1, wherein the step of contacting comprises incubating each of the encoded small molecules with each of the first and second variants in series.

10. The method of claim 1, wherein the library is a DNA-encoded library.

11. The method of claim 10 further comprising amplifying the DNA codons of DNA encoded agents with PCR.

12. The method of claim 11 further comprising sequencing the PCR amplified DNA.

13. The method of claim 12, wherein the step of determining binding comprises measuring the relative or absolute library member sequence abundance for the small molecule DNA coding sequences.

14. The method of claim 13, wherein the step of determining binding comprises measuring an enrichment of post-selection sequence abundance for the small molecule codons over preselection sequence abundance.

15. The method of claim 14, wherein the step of comparing comprises comparing the measured enrichment in sequence abundance for each small molecule after incubation with the first variant with the measured enrichment in sequence abundance after incubation with the second variant.

16. The method of claim 1, wherein the protein is insulin degrading enzyme (IDE).

17. The method of claim 11, wherein PCR primers are used to amplify DNA.

* * * * *

SEQUENCE LISTING

<160> NUMBER OF SEQ ID NOS: 13

<210> SEQ ID NO 1
<211> LENGTH: 1019
<212> TYPE: PRT
<213> ORGANISM: Homo sapiens

<400> SEQUENCE: 1

```
Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Glu Arg Leu Cys
            20                  25                  30

Gly Phe Gln Lys Lys Thr Tyr Ser Lys Met Asn Asn Pro Ala Ile Lys
                35                  40                  45

Arg Ile Gly Asn His Ile Thr Lys Ser Pro Glu Asp Lys Arg Glu Tyr
        50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
    210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
        275                 280                 285

Pro Glu His Pro Phe Gln Glu Glu His Leu Lys Gln Leu Tyr Lys Ile
    290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
            340                 345                 350

Lys Gly Trp Val Asn Thr Leu Val Gly Gly Gln Lys Glu Gly Ala Arg
        355                 360                 365
```

```
Gly Phe Met Phe Phe Ile Ile Asn Val Asp Leu Thr Glu Glu Gly Leu
        370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
            420                 425                 430

Tyr Thr Ser Lys Ile Ala Gly Ile Leu His Tyr Tyr Pro Leu Glu Glu
            435                 440                 445

Val Leu Thr Ala Glu Tyr Leu Leu Glu Glu Phe Arg Pro Asp Leu Ile
450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
                485                 490                 495

Gly Thr Gln Tyr Lys Gln Glu Ala Ile Pro Asp Glu Val Ile Lys Lys
                500                 505                 510

Trp Gln Asn Ala Asp Leu Asn Gly Lys Phe Lys Leu Pro Thr Lys Asn
            515                 520                 525

Glu Phe Ile Pro Thr Asn Phe Glu Ile Leu Pro Leu Glu Lys Glu Ala
530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
                565                 570                 575

Glu Phe Phe Ser Pro Phe Ala Tyr Val Asp Pro Leu His Cys Asn Met
                580                 585                 590

Ala Tyr Leu Tyr Leu Glu Leu Leu Lys Asp Ser Leu Asn Glu Tyr Ala
            595                 600                 605

Tyr Ala Ala Glu Leu Ala Gly Leu Ser Tyr Asp Leu Gln Asn Thr Ile
610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
                645                 650                 655

Lys Arg Phe Glu Ile Ile Lys Glu Ala Tyr Met Arg Ser Leu Asn Asn
                660                 665                 670

Phe Arg Ala Glu Gln Pro His Gln His Ala Met Tyr Tyr Leu Arg Leu
            675                 680                 685

Leu Met Thr Glu Val Ala Trp Thr Lys Asp Glu Leu Lys Glu Ala Leu
690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Ile Met Gln Met Val Glu Asp Thr Leu Ile Glu His
            740                 745                 750

Ala His Thr Lys Pro Leu Leu Pro Ser Gln Leu Val Arg Tyr Arg Glu
            755                 760                 765

Val Gln Leu Pro Asp Arg Gly Trp Phe Val Tyr Gln Arg Asn Glu
770                 775                 780

Val His Asn Asn Cys Gly Ile Glu Ile Tyr Tyr Gln Thr Asp Met Gln
```

```
            785                 790                 795                 800
    Ser Thr Ser Glu Asn Met Phe Leu Glu Leu Phe Cys Gln Ile Ile Ser
                        805                 810                 815

Glu Pro Cys Phe Asn Thr Leu Arg Thr Lys Glu Gln Leu Gly Tyr Ile
                        820                 825                 830

Val Phe Ser Gly Pro Arg Arg Ala Asn Gly Ile Gln Gly Leu Arg Phe
                        835                 840                 845

Ile Ile Gln Ser Glu Lys Pro Pro His Tyr Leu Glu Ser Arg Val Glu
                850                 855                 860

Ala Phe Leu Ile Thr Met Glu Lys Ser Ile Glu Asp Met Thr Glu Glu
    865                 870                 875                 880

Ala Phe Gln Lys His Ile Gln Ala Leu Ala Ile Arg Arg Leu Asp Lys
                        885                 890                 895

Pro Lys Lys Leu Ser Ala Glu Cys Ala Lys Tyr Trp Gly Glu Ile Ile
                        900                 905                 910

Ser Gln Gln Tyr Asn Phe Asp Arg Asp Asn Thr Glu Val Ala Tyr Leu
                915                 920                 925

Lys Thr Leu Thr Lys Glu Asp Ile Ile Lys Phe Tyr Lys Glu Met Leu
                930                 935                 940

Ala Val Asp Ala Pro Arg Arg His Lys Val Ser Val His Val Leu Ala
    945                 950                 955                 960

Arg Glu Met Asp Ser Cys Pro Val Val Gly Glu Phe Pro Cys Gln Asn
                        965                 970                 975

Asp Ile Asn Leu Ser Gln Ala Pro Ala Leu Pro Gln Pro Glu Val Ile
                980                 985                 990

Gln Asn Met Thr Glu Phe Lys Arg Gly Leu Pro Leu Phe Pro Leu Val
                995                 1000                1005

Lys Pro His Ile Asn Phe Met Ala Ala Lys Leu
                1010                1015

<210> SEQ ID NO 2
<211> LENGTH: 464
<212> TYPE: PRT
<213> ORGANISM: Homo sapiens

<400> SEQUENCE: 2

Met Ser Lys Leu Trp Phe Lys Gln Asp Asp Lys Phe Phe Leu Pro Lys
    1               5                   10                  15

Ala Cys Leu Asn Phe Glu Phe Phe Ser Pro Phe Ala Tyr Val Asp Pro
                        20                  25                  30

Leu His Cys Asn Met Ala Tyr Leu Tyr Leu Glu Leu Leu Lys Asp Ser
                        35                  40                  45

Leu Asn Glu Tyr Ala Tyr Ala Ala Glu Leu Ala Gly Leu Ser Tyr Asp
                50                  55                  60

Leu Gln Asn Thr Ile Tyr Gly Met Tyr Leu Ser Val Lys Gly Tyr Asn
    65                  70                  75                  80

Asp Lys Gln Pro Ile Leu Leu Lys Lys Ile Ile Glu Lys Met Ala Thr
                        85                  90                  95

Phe Glu Ile Asp Glu Lys Arg Phe Glu Ile Ile Lys Glu Ala Tyr Met
                        100                 105                 110

Arg Ser Leu Asn Asn Phe Arg Ala Glu Gln Pro His Gln His Ala Met
                        115                 120                 125

Tyr Tyr Leu Arg Leu Leu Met Thr Glu Val Ala Trp Thr Lys Asp Glu
                130                 135                 140
```

```
Leu Lys Glu Ala Leu Asp Asp Val Thr Leu Pro Arg Leu Lys Ala Phe
145                 150                 155                 160

Ile Pro Gln Leu Leu Ser Arg Leu His Ile Glu Ala Leu Leu His Gly
            165                 170                 175

Asn Ile Thr Lys Gln Ala Ala Leu Gly Ile Met Gln Met Val Glu Asp
        180                 185                 190

Thr Leu Ile Glu His Ala His Thr Lys Pro Leu Leu Pro Ser Gln Leu
    195                 200                 205

Val Arg Tyr Arg Glu Val Gln Leu Pro Asp Arg Gly Trp Phe Val Tyr
210                 215                 220

Gln Gln Arg Asn Glu Val His Asn Asn Cys Gly Ile Glu Ile Tyr Tyr
225                 230                 235                 240

Gln Thr Asp Met Gln Ser Thr Ser Glu Asn Met Phe Leu Glu Leu Phe
                245                 250                 255

Cys Gln Ile Ile Ser Glu Pro Cys Phe Asn Thr Leu Arg Thr Lys Glu
            260                 265                 270

Gln Leu Gly Tyr Ile Val Phe Ser Gly Pro Arg Arg Ala Asn Gly Ile
        275                 280                 285

Gln Gly Leu Arg Phe Ile Ile Gln Ser Glu Lys Pro Pro His Tyr Leu
    290                 295                 300

Glu Ser Arg Val Glu Ala Phe Leu Ile Thr Met Glu Lys Ser Ile Glu
305                 310                 315                 320

Asp Met Thr Glu Glu Ala Phe Gln Lys His Ile Gln Ala Leu Ala Ile
                325                 330                 335

Arg Arg Leu Asp Lys Pro Lys Lys Leu Ser Ala Glu Cys Ala Lys Tyr
            340                 345                 350

Trp Gly Glu Ile Ile Ser Gln Gln Tyr Asn Phe Asp Arg Asp Asn Thr
        355                 360                 365

Glu Val Ala Tyr Leu Lys Thr Leu Thr Lys Glu Asp Ile Ile Lys Phe
    370                 375                 380

Tyr Lys Glu Met Leu Ala Val Asp Ala Pro Arg Arg His Lys Val Ser
385                 390                 395                 400

Val His Val Leu Ala Arg Glu Met Asp Ser Cys Pro Val Val Gly Glu
                405                 410                 415

Phe Pro Cys Gln Asn Asp Ile Asn Leu Ser Gln Ala Pro Ala Leu Pro
            420                 425                 430

Gln Pro Glu Val Ile Gln Asn Met Thr Glu Phe Lys Arg Gly Leu Pro
        435                 440                 445

Leu Phe Pro Leu Val Lys Pro His Ile Asn Phe Met Ala Ala Lys Leu
450                 455                 460

<210> SEQ ID NO 3
<211> LENGTH: 1019
<212> TYPE: PRT
<213> ORGANISM: Mus musculus

<400> SEQUENCE: 3

Met Arg Asn Gly Leu Val Trp Leu Leu His Pro Ala Leu Pro Gly Thr
1               5                   10                  15

Leu Arg Ser Ile Leu Gly Ala Arg Pro Pro Ala Lys Arg Leu Cys
            20                  25                  30

Gly Phe Pro Lys Gln Thr Tyr Ser Thr Met Ser Asn Pro Ala Ile Gln
        35                  40                  45

Arg Ile Glu Asp Gln Ile Val Lys Ser Pro Glu Asp Lys Arg Glu Tyr
    50                  55                  60
```

```
Arg Gly Leu Glu Leu Ala Asn Gly Ile Lys Val Leu Leu Ile Ser Asp
 65                  70                  75                  80

Pro Thr Thr Asp Lys Ser Ser Ala Ala Leu Asp Val His Ile Gly Ser
                 85                  90                  95

Leu Ser Asp Pro Pro Asn Ile Pro Gly Leu Ser His Phe Cys Glu His
            100                 105                 110

Met Leu Phe Leu Gly Thr Lys Lys Tyr Pro Lys Glu Asn Glu Tyr Ser
            115                 120                 125

Gln Phe Leu Ser Glu His Ala Gly Ser Ser Asn Ala Phe Thr Ser Gly
130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Ala
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
            195                 200                 205

Gly Asn Pro Lys His Pro Phe Ser Lys Phe Gly Thr Gly Asn Lys Tyr
210                 215                 220

Thr Leu Glu Thr Arg Pro Asn Gln Glu Gly Ile Asp Val Arg Glu Glu
225                 230                 235                 240

Leu Leu Lys Phe His Ser Thr Tyr Tyr Ser Ser Asn Leu Met Ala Ile
                245                 250                 255

Cys Val Leu Gly Arg Glu Ser Leu Asp Asp Leu Thr Asn Leu Val Val
            260                 265                 270

Lys Leu Phe Ser Glu Val Glu Asn Lys Asn Val Pro Leu Pro Glu Phe
            275                 280                 285

Pro Glu His Pro Phe Gln Glu Glu His Leu Arg Gln Leu Tyr Lys Ile
            290                 295                 300

Val Pro Ile Lys Asp Ile Arg Asn Leu Tyr Val Thr Phe Pro Ile Pro
305                 310                 315                 320

Asp Leu Gln Gln Tyr Tyr Lys Ser Asn Pro Gly His Tyr Leu Gly His
                325                 330                 335

Leu Ile Gly His Glu Gly Pro Gly Ser Leu Leu Ser Glu Leu Lys Ser
            340                 345                 350

Lys Gly Trp Val Asn Thr Leu Val Gly Gly Gln Lys Glu Gly Ala Arg
            355                 360                 365

Gly Phe Met Phe Phe Ile Ile Asn Val Asp Leu Thr Glu Glu Gly Leu
            370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
                405                 410                 415

Leu Asn Ala Val Ala Phe Arg Phe Lys Asp Lys Glu Arg Pro Arg Gly
            420                 425                 430

Tyr Thr Ser Lys Ile Ala Gly Lys Leu His Tyr Tyr Pro Leu Asn Gly
            435                 440                 445

Val Leu Thr Ala Glu Tyr Leu Leu Glu Glu Phe Arg Pro Asp Leu Ile
            450                 455                 460

Asp Met Val Leu Asp Lys Leu Arg Pro Glu Asn Val Arg Val Ala Ile
465                 470                 475                 480
```

-continued

```
Val Ser Lys Ser Phe Glu Gly Lys Thr Asp Arg Thr Glu Gln Trp Tyr
                485                 490                 495
Gly Thr Gln Tyr Lys Gln Glu Ala Ile Pro Glu Asp Ile Ile Gln Lys
            500                 505                 510
Trp Gln Asn Ala Asp Leu Asn Gly Lys Phe Lys Leu Pro Thr Lys Asn
        515                 520                 525
Glu Phe Ile Pro Thr Asn Phe Glu Ile Leu Ser Leu Glu Lys Asp Ala
    530                 535                 540
Thr Pro Tyr Pro Ala Leu Ile Lys Asp Thr Ala Met Ser Lys Leu Trp
545                 550                 555                 560
Phe Lys Gln Asp Asp Lys Phe Leu Pro Lys Ala Cys Leu Asn Phe
                565                 570                 575
Glu Phe Phe Ser Pro Phe Ala Tyr Val Asp Pro Leu His Cys Asn Met
            580                 585                 590
Ala Tyr Leu Tyr Leu Glu Leu Leu Lys Asp Ser Leu Asn Glu Tyr Ala
        595                 600                 605
Tyr Ala Ala Glu Leu Ala Gly Leu Ser Tyr Asp Leu Gln Asn Thr Ile
    610                 615                 620
Tyr Gly Met Tyr Leu Ser Val Lys Gly Tyr Asn Asp Lys Gln Pro Ile
625                 630                 635                 640
Leu Leu Lys Lys Ile Thr Glu Lys Met Ala Thr Phe Glu Ile Asp Lys
                645                 650                 655
Lys Arg Phe Glu Ile Ile Lys Glu Ala Tyr Met Arg Ser Leu Asn Asn
            660                 665                 670
Phe Arg Ala Glu Gln Pro His Gln His Ala Met Tyr Tyr Leu Arg Leu
        675                 680                 685
Leu Met Thr Glu Val Ala Trp Thr Lys Asp Glu Leu Lys Glu Ala Leu
    690                 695                 700
Asp Asp Val Thr Leu Pro Arg Leu Lys Ala Phe Ile Pro Gln Leu Leu
705                 710                 715                 720
Ser Arg Leu His Ile Glu Ala Leu Leu His Gly Asn Ile Thr Lys Gln
                725                 730                 735
Ala Ala Leu Gly Val Met Gln Met Val Glu Asp Thr Leu Ile Glu His
            740                 745                 750
Ala His Thr Lys Pro Leu Leu Pro Ser Gln Leu Val Arg Tyr Arg Glu
        755                 760                 765
Val Gln Leu Pro Asp Arg Gly Trp Phe Val Tyr Gln Gln Arg Asn Glu
    770                 775                 780
Val His Asn Asn Cys Gly Ile Glu Ile Tyr Tyr Gln Thr Asp Met Gln
785                 790                 795                 800
Ser Thr Ser Glu Asn Met Phe Leu Glu Leu Phe Cys Gln Ile Ile Ser
                805                 810                 815
Glu Pro Cys Phe Asn Thr Leu Arg Thr Lys Glu Gln Leu Gly Tyr Ile
            820                 825                 830
Val Phe Ser Gly Pro Arg Arg Ala Asn Gly Ile Gln Gly Leu Arg Phe
        835                 840                 845
Ile Ile Gln Ser Glu Lys Pro Pro His Tyr Leu Glu Ser Arg Val Glu
    850                 855                 860
Ala Phe Leu Ile Thr Met Glu Lys Ala Ile Glu Asp Met Thr Glu Glu
865                 870                 875                 880
Ala Phe Gln Lys His Ile Gln Ala Leu Ala Ile Arg Arg Leu Asp Lys
                885                 890                 895
Pro Lys Lys Leu Ser Ala Glu Cys Ala Lys Tyr Trp Gly Glu Ile Ile
```

```
                       900                 905                 910
Ser Gln Gln Tyr Asn Tyr Asp Arg Asp Asn Ile Glu Val Ala Tyr Leu
            915                 920                 925

Lys Thr Leu Thr Lys Asp Asp Ile Ile Arg Phe Tyr Gln Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Ser Gln Asn
                965                 970                 975

Asp Ile Asn Leu Ser Glu Ala Pro Pro Leu Pro Gln Pro Glu Val Ile
            980                 985                 990

His Asn Met Thr Glu Phe Lys Arg  Gly Leu Pro Leu Phe  Pro Leu Val
        995                 1000                1005

Lys Pro  His Ile Asn Phe Met  Ala Ala Lys Leu
    1010                1015
```

<210> SEQ ID NO 4
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: U is deoxyuridine

<400> SEQUENCE: 4
atcatcatat gaataatcca gccaucaaga gaatagg                              37

<210> SEQ ID NO 5
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(21)
<223> OTHER INFORMATION: U is deoxyuridine

<400> SEQUENCE: 5
atgctagcca tacctcagag utttgcagcc atgaag                               36

<210> SEQ ID NO 6
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: U is deoxyuridine

<400> SEQUENCE: 6
atggctggat tattcatatg atgaugatga tgatgagaac cc                        42

<210> SEQ ID NO 7
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:

<221> NAME/KEY: misc_feature
<222> LOCATION: (21)..(21)
<223> OTHER INFORMATION: U is deoxyuridine

<400> SEQUENCE: 7
actctgaggt atggctagca ugactggtg                              29

<210> SEQ ID NO 8
<211> LENGTH: 45
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (27)..(27)
<223> OTHER INFORMATION: U is deoxyuridine

<400> SEQUENCE: 8
atgtccgggt tctgatagtt tctaaauctt ttgaaggaaa aactg            45

<210> SEQ ID NO 9
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (27)..(27)
<223> OTHER INFORMATION: U is deoxyuridine

<400> SEQUENCE: 9
atttagaaac tatcagaacc cggacauttt ctggtctgag                  40

<210> SEQ ID NO 10
<211> LENGTH: 48
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(38)
<223> OTHER INFORMATION: N may be absent

<400> SEQUENCE: 10
acactctttc cctacacgac gctcttccga tctnnnnnga gtgggatg         48

<210> SEQ ID NO 11
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 11
tggagttcag acgtgtgctc ttccgatctc cctgtacac                   39

<210> SEQ ID NO 12
<211> LENGTH: 52
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(25)
<223> OTHER INFORMATION: modified by a 7-base identifier

```
<400> SEQUENCE: 12
caagcagaag acggcatacg agatgtgact ggagttcaga cgtgtgctct tc          52

<210> SEQ ID NO 13
<211> LENGTH: 49
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (29)..(30)
<223> OTHER INFORMATION: modified by a 7-base identifier

<400> SEQUENCE: 13
aatgatacgg cgaccaccga gatctacaca cactctttcc ctacacgac              49
```